United States Patent [19]

Bey et al.

[11] Patent Number: 4,866,206

[45] Date of Patent: Sep. 12, 1989

[54] 2-HALOMETHYL DERIVATIVES OF 2-AMINO ACIDS

[75] Inventors: Philippe Bey, Strasbourg; Michel Jung, Illkirch-Graffenstaden, both of France

[73] Assignee: Merrell Dow France et Cie, Strasbourg, France

[21] Appl. No.: 148,806

[22] Filed: Jan. 27, 1988

Related U.S. Application Data

[60] Division of Ser. No. 392,052, Jun. 25, 1982, Pat. No. 4,743,691, which is a continuation-in-part of Ser. No. 53,937, Jul. 2, 1979, abandoned, which is a continuation of Ser. No. 814,765, Jul. 11, 1977, abandoned.

[51] Int. Cl.$^4$ ............................................. C07C 99/00
[52] U.S. Cl. ..................................................... 562/561
[58] Field of Search ................................ 562/561, 574

[56] References Cited

U.S. PATENT DOCUMENTS

| | | | |
|---|---|---|---|
| 4,288,601 | 9/1981 | Kollonitsch | 562/561 |
| 4,325,961 | 4/1982 | Kollonitsch | 562/561 |
| 4,418,077 | 11/1983 | Bey | 562/561 |
| 4,423,073 | 12/1983 | Gerhart | 562/561 |
| 4,439,619 | 3/1984 | Bey | 562/561 |
| 4,446,151 | 5/1984 | Gerhart | 562/561 |

*Primary Examiner*—Michael L. Shippen
*Attorney, Agent, or Firm*—Louis J. Wille

[57] ABSTRACT

2-(Fluoromethyl or chloromethyl)-2,5-diaminopentanoic acid, 2-(fluoromethyl or chloromethyl)-2,6-diaminohexanoic acid, and 2-fluoromethyl-2-amino-5-guanidinopentanoic acid, and certain derivatives thereof, are inhibitors of ornithine decarboxylase. Methods of preparing the compounds and derivatives are also described.

4 Claims, No Drawings

2-HALOMETHYL DERIVATIVES OF 2-AMINO ACIDS

CROSS-REFERENCE TO RELATED APPLICATION

This is a division of application Ser. No. 392,052 filed June 25, 1982, now U.S. Pat. No. 4,743,691, which is a continuation-in-part of pending application Serial No. 53,937, filed July 2, 1979, now abandoned, which is a continuation of application Serial No. 814,765, filed July 11, 1977, now abandoned.

The present invention relates to 2-(fluoromethyl or chloromethyl)-2,5-diaminopentanoic acid and to 2-(fluoromethyl or chloromethyl)-2,6-diaminohexanoic acid, and to derivatives thereof, which compounds in vivo are inhibitors of ornithine decarboxylase, an enzyme which is involved in polyamine formation in organisms. The invention also provides pharmaceutical compositions comprising said compounds, methods of medical treatment using said compounds, and processes for preparing said compounds.

In both eukaryotic and prokaryotic cells, the decarboxylation of ornithine to putrescine, a reaction catalyzed by ornithine decarboxylase (ODC), is the first step in the biosynthesis of the polyamines known as spermidine and spermine. Spermidine is formed by the transfer of an activated aminopropyl moiety from S-adenosyl S-methyl homocysteamine to putrescine, while spermine is formed by the transfer of a second aminopropyl group to spermidine. Ornithine is formed from arginine by the action of arginase. S-Adenosyl S-methyl homocysteamine is formed by the decarboxylation of S-adenosylmethionine (SAM), a reaction catalyzed by the enzyme S-adenosylmethionine decarboxylase (SAMDC). In mammals, lysine is also decarboxylated by ODC. In prokaryotic cells, lysine is decarboxylated by lysine decarboxylase.

In prokaryotic cells and in plant cells, putrescine can also be biosynthesized via an alternative pathway which involves the decarboxylation of arginine by arginine decarboxylase to yield agmatine and the conversion of agmatine to putrescine.

The polyamines, which are found in animal tissues and microorganisms, are known to play an important role in cell growth and proliferation. The onset of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis.

Since, in eukaryotic cells, putrescine is a precursor of the polyamines spermidine and spermine, blockage of the conversion of ornithine to putrescine, such as by inhibition of ODC, will prevent new biosynthesis of these polyamines. However, the continuous synthesis of these polyamines is not vital to cell viability, provided the preexisting polyamine pool is maintained above a certain critical level. Moreover, total blockage of polyamine biosynthesis by inhibition of ODC will be difficult to maintain because of the high turnover rate of this enzyme. Nevertheless, we have found that blockage of the conversion of ornithine to putrescine according to this invention can have beneficial effects in certain cell proliferation situations, to be hereinafter discussed.

In its first composition of matter aspect, the invention sought to be patented comprehends a pharmacologically active chemical compound of the formula:

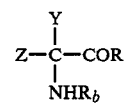

wherein:

Z is $\gamma$-guanidinopropyl or $R_a NH(CH_2)_n$— wherein $R_a$ is hydrogen, $(C_1-C_4)$alkylcarbonyl, or the group

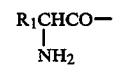

wherein $R_1$ is $(C_1-C_4)$alkyl, benzyl, or p-hydroxybenzyl;

Y is —CH$_2$F or —CH$_2$Cl;

$R_b$ is hydrogen or $(C_1-C_4)$alkylcarbonyl; and

R is hydroxy or $(C_1-C_8)$alkoxy;

or a pharmaceutically acceptable salt thereof; or an individual optical isomer thereof; with the provisos that:

(a) when A is $\gamma$-guanidinopropyl, Y is —CH$_2$F, $R_b$ is hydrogen, and R is hydroxy;

(b) when Y is —CH$_2$Cl, Z is $R_a NH(CH_2)_n$— wherein $R_a$ is hydrogen and n is 3 or 4, and $R_b$ is hydrogen; and (c) when $R_b$ is $(C_1-C_4)$alkylcarbonyl, Z is $R_a NH(CH_2)_n$— wherein $R_a$ is hydrogen and n is 3 or 4, and R is hydroxy.

As employed herein, "$(C_1-C_4)$alkyl" means a straight or branched alkyl group having 1 to 4 carbon atoms. Examples of $(C_1-C_4)$alkyl groups are methyl, ethyl, n-propyl, n-butyl, isopropyl, and tert-butyl.

As employed herein, "$(C_1-C_8)$alkoxy" means a group of the formula -O-alkyl, wherein the alkyl moiety is straight or branched and contains from 1 to 8 carbon atoms. Examples of $(C_1-C_8)$alkoxy groups are methoxy, propoxy, n-butoxy, tert-butoxy, pentyloxy, and octyloxy.

As employed herein, "$(C_1-C_4)$alkylcarbonyl" means a group of the formula

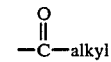

wherein the alkyl moiety is straight or branched and contains from 1 to 4 carbon atoms. Examples of $(C_1-C_4)$alkylcarbonyl groups are acetyl, propionyl, i-butyroyl, or tert-butyroyl.

As employed herein, the group represented by the formula $R_1 CH(NH_2)CO$— is an aminocarboxylic acid residue derived by removing the hydroxy group from the carboxy moiety of the appropriate amino acid, for example: glycine, alanine, valine, leucine, isoleucine, phenylalanine, or tyrosine. Preferably, amino acid residues are in the natural or L-configuration.

Preferred $(C_1-C_8)$alkoxy groups are ethoxy and tert-butoxy. The preferred $(C_1-C_4)$alkylcarbonyl group is acetyl.

Illustrative examples of pharmaceutically acceptable salts of the compounds of Formula I include non-toxic acid addition salts formed with inorganic acids, such as hydrochloric, hydrobromic, sulfuric, and phosphoric acid, and organic acids, such as methane sulfonic, salicylic, maleic, malonic, tartaric, citric, cyclamic, and ascorbic acids; and non-toxic salts formed with inorganic or organic bases, such as those of alkali metals, for example, sodium, potassium, and lithium, alkaline earth metals, for example, calcium and magnesium, light metals of Group III A, for example aluminium, organic amines, such as primary, secondary, or tertiary amines, for example, cyclohexylamine, ethylamine, pyridine, methylaminoethanol, ethanolamine, and piperazine. The salts are prepared by conventional means.

When in Formula I, Z is $R_aHN-(CH_2)_n-$, wherein $R_a$ is hydrogen and n is 3, and R is $(C_1-C_8)$alkoxy, it is preferable to obtain and purify the compounds in the form of a di-acid addition salt, such as the dihydrochloride salt, since protonation of the sidechain amino group lessens lactam formation.

In Formula I, Z is either $R_aHN-(CH_2)_n-$, wherein n is 3 or 4, or $\gamma$-guanidinopropyl. Accordingly, (a) when Z is $R_aHN-(CH_2)_n-$, the compounds are 2-(fluoromethyl or chloromethyl)-2,5-diaminopentanoic acid, or derivatives thereof, or 2-(fluoromethyl or chloromethyl)-2,6-diminohexanoic acid, or derivatives thereof, depending upon whether n is 3 or 4, respectively; and (b) when Z is $\gamma$-guanidinopropyl, the compound is 2-fluoromethyl-2-amino-5-guanidinopentanoic acid.

2-(Fluoromethyl or chloromethyl)-2,5-diaminopentanoic acid can also be named as 2-(fluoromethyl or chloromethyl)-2,5-diaminovaleric acids or as $\alpha$-(fluoromethyl or chloromethyl)-ornithine. The abbreviation "$\alpha$-MFM" may also be employed to refer to $\alpha$-(fluoromethyl)ornithine. 2-(Fluoromethyl or chloromethyl)-2,6-diaminohexanoic acid can also be named as 2-(fluoromethyl or chloromethyl)-2,6-caproic acid or as $\alpha$-(fluoromethyl or chloromethyl)lysine. 2-Fluoromethyl-2-amino-5-guanidinopentanoic acid can also be named $\alpha$-fluoromethylarginine.

Preferably, in Formula I, Y is $-CH_2F$; Z is $R_aHN-(CH_2)_n-$ wherein n is 3, and $R_a$ is hydrogen, $(C_1-C_4)$alkylcarbonyl, or $R_1CH(NH_2)CO-$, wherein $R_1$ is hydrogen, $(C_1-C_4)$alkyl, benzyl, or p-hydroxybenzyl; $R_b$ is hydrogen; and R is hydroxy or $(C_1-C_8)$alkoxy. Most preferably, $R_a$ is hydrogen and R is hydroxy.

In subgeneric aspects of Formula I, the invention provides the following embodiments:

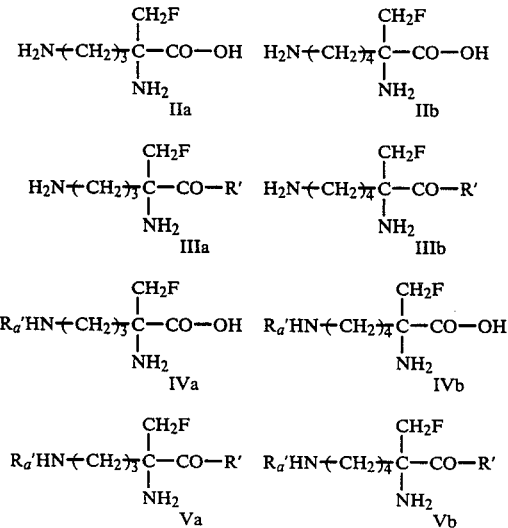

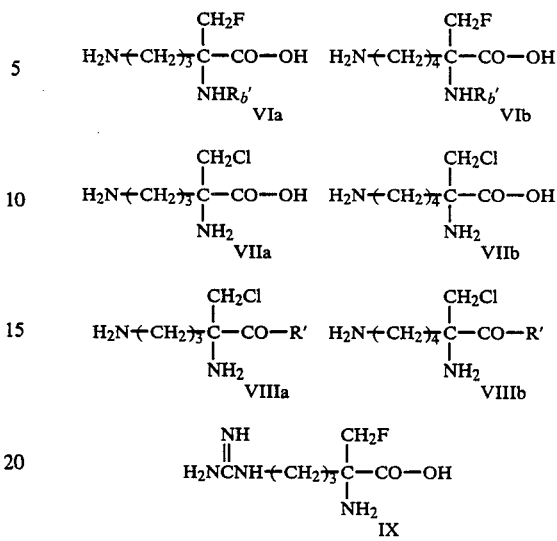

In Formula IIIa, IIIb, Va, Vb, VIIIa and VIIIb, R' is $(C_1-C_8)$alkoxy. In Formula IVa, IVb, Va, and Vb, $R_a'$ is $(C_1-C_4)$alkylcarbonyl or $R_1CH(NH_2)CO-$, wherein $R_1$ is hydrogen, $(C_1-C_4)$alkyl, benzyl, or p-hydroxybenzyl. In Formula VIa or VIb, $R'_a$ is $(C_1-C_4)$alkylcarbonyl.

Preferred embodiments are those represented by Formula IIa, IIIa, IVa, Va, and VIa. Most preferred embodiments are those of Formula IIa and Va.

Illustrative examples of the compounds of Formula I are:

2-fluoromethyl-2,5-diaminopentanoic acid,
2-fluoromethyl-2,6-diaminohexanoic acid, ethyl 2-fluoromethyl-2,5-diminopentanoate tert-butyl 2-fluoromethyl-2,5-diaminopentanoate,
2-chloromethyl-2,5-diaminopentanoic acid,
2-chloromethyl-2,6-diaminohexanoic acid,
2-fluoromethyl-2-amino-5-guanidinopentanoic acid.

The compounds of Formula I inhibit ornithine decarboxylase enzyme (ODC) in vivo, and produce a decrease of putrescine and spermidine concentrations in cells in which active biosynthesis of polyamines is taking place. Therefore, they can be employed in specific situations to control cell growth or proliferation.

In particular, 2-fluoromethyl-2,5-diaminopentanoic acid has been found to be capable of interrupting embryogenesis in female mice when tested by the general method described by J. Fozard, *European Journal of Pharmacology*, 65, 379 (1980). Accordingly, the compounds of Formula I can be used as contragestational agents (abortifacients) in female animals when it is desired to terminate early pregnancy. The use of 2-fluoromethyl-2,5-diaminopentanoic acid, and derivatives thereof, as a contragestational agent is described and claimed in U.S. Pat. No. 4,309,442 of P. Bey and M. Jung. In addition, 2-fluoromethyl-2,5-diamino-pentanoic acid has also been found to be capable of producing a significant decrease in weight of the ventral prostate in rats when tested by the general method described by C. Danzin et al., *Biochem. J.*, 202, 175 (1982). Accordingly, the compounds of Formula I can be used to treat benign prostatic hypertrophy. The use of 2-fluoromethyl-2,5-diaminopentanoic acid, and derivatives thereof, in the treatment of benign prostatic hypertrophy is described and claimed in the U.S. Pat. No. 4,330,559 of P. Bey and M. Jung.

The ODC inhibitory activity of a compound can be determined in vitro by the method described by B. Metcalf et al., *J. Am. Chem. Soc.*, 100, 2551 (1978) and in vivo by the method of C. Danzin, *Life Sciences*, 24, 519 (1979).

The in vitro inhibition of rat liver ODC by 2-fluoromethyl-2,5-diaminopentanoic acid, 2-chloromethyl-2,5-diaminopentanoic acid, 2-fluoromethyl2,6-diaminohexanoic acid, and 2-chloromethyl-2,6-diaminohexanoic acid is described herein in Example 10. The in vivo inhibition ODC in the ventral prostate or thymus of rats by 2-fluoromethyl-2,5-diaminopentanoic acid and 2-fluoromethyl-2,5-diaminohexanoic acid is described herein in Example 11.

2- Fluoromethyl-2,5-diaminopentanoic acid (α-MFM) has been found to inhibit ODC of E. coli and P. aeruginosa in vitro and in intact cells. However, by itself, α-MFMO has no effect on cell growth. Thus, ornithine carboxylase inhibitory activity is useful only when used in combination with agents which will block other routes of polyamine biosynthesis, e.g. with both (a) α-difluoromethyl arginine, which inhibits arginine decarboxylase, and (b) dicyclohexylammonium sulfate, which inhibits spermidine synthesis.

While 2-fluoromethyl-2,5-diaminopentanoic acid functions to slow rather than stop neoplastic cell proliferation, it is believed that the best manner of using 2-fluoromethyl-2,5-diaminopentanoic acid for the treatment of neoplasms, generally, will be in conjunction with cytotoxic agents.

The following publications report the in vitro ODC inhibitory properties of 2-fluoromethyl-2,5-diaminopentanoic acid:

(a) toward rat liver ODC: P. Bey, *Enzyme-Activated Irreversible Inhibitor,*; N. Seiler, Ed., Elsevier/North Holland, Amsterdam, 1978, pages 27 to 41 and (b) toward ODC from *Trypanosoma brucei:* D. Hope et al., *Federation Proceedings,* Vol. 41, No. 4, Abstract No. 5282, 1982.

The following publications report the in vitro rat liver ODC inhibitory properties of 2-chloromethyl-2,5-diaminopentanoic acid:

(a) B. Metcalf et al., J. Am. Chem. Soc., 100, 2551 (1978), and (b) P. Bey, *Enzyme-Activated Irreversible Inhibition,* ibidem.

When, in Formula I, Z is $R_aHN-(CH_2)_n-$ and $R_a$ or $R_b$ is a group other than hydrogen, or R is a group other than hydroxy, such compounds do not inhibit ODC enzyme in vitro. In order to produce ODC inhibition in vivo, such compounds must be capable of undergoing biotransformation (either non-enzymatically or enzymatically) to give the compounds wherein $R_a$ and $R_b$ are both hydrogen and R is hydroxy [i.e. 2-(fluoromethyl or chloromethyl)-2,5-diaminopentanoic acid or 2-(fluoromethyl or chloromethyl)-2,6-diaminohexanoic acid], which compounds will inhibit ODC both in vitro and in vivo.

2-Fluoromethyl-2-amino-5-guanidinopentanoic acid (α-gluoromethylarginine) will not inhibit ODC in vitro. In order to produce inhibition of ODC in vivo, the compound must be capable of undergoing biotransformation by arginase to give 2-fluoromethyl 2,5-diaminpentanoic acid (α-fluoromethylornithine), which will inhibit ODC both in vitro and in vivo.

When, in Formula I, Z is $R_aHN-(CH_2)_n-$, wherein n is 4, the compounds will also inhibit bacterial lysine decarboxylase. When in Formula I, Z is γ-guanidinopropyl, the compounds will also inhibit bacterial arginine decarboxylase. Both lysine decarboxylase and arginine decarboxylase are not involved in mammalian polyamine formation.

In its second composition of matter aspect, the present invention comprehends a chemical compound of the formula:

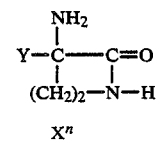

wherein Y is $-CH_2F$ or $-CH_2Cl$ and n is 3 to 4. The compounds of Formula X are useful as intermediates for preparing 2-(fluoromethyl or chloromethyl)-2,5-diaminopentanoic acid, when n is 3, and 2-(fluoromethyl or chloromethyl)-2,6-diaminohexanoic acid, when n is 4. A preferred embodiment of Formula X is 3-amino-3-fluoromethyl-2-piperidone which is especially useful for preparing the individual (+)-enantiomer enantiomer and (−)-enantiomer of 2-fluoromethyl-2,5-diaminopentanoic acid, using the general method of R. Viterbo et al., *Tetrahedron Letters,* 48, 4617 (1971).

2-Fluoromethyl-2,5-diaminopentanoic acid (Formula IIa), 2-fluoromethyl-2,6-diaminohexanoic acid (Formula IIb), 2-chloromethyl-2,5-diaminopentanoic acid (Formula VIIIa), and 2-chloromethyl-2,6-diaminohexanoic acid (Formula VIIIb) can be prepared by:

(a) treating 2,5-diaminopentanoic acid (ornithine) or 2,6-diaminohexanoic acid (lysine), wherein the carboxy group and the amino groups are protected with a strong base to form the carbanion intermediate;

(b) reacting the carbanion intermediate with a suitablehalomethyl-halo alkylating reagent in an aprotic solvent in the presence of hexamethylphosphoramide at a temperature of about −120° C. to 120° C., preferably about 25° to 50° C., and a reaction time of about ½ hour to 48 hours; and (c) hydrolyzing the protected α-halomethyl ornithine or lysine compound. The reaction sequence is shown schematically below:

SCHEME A

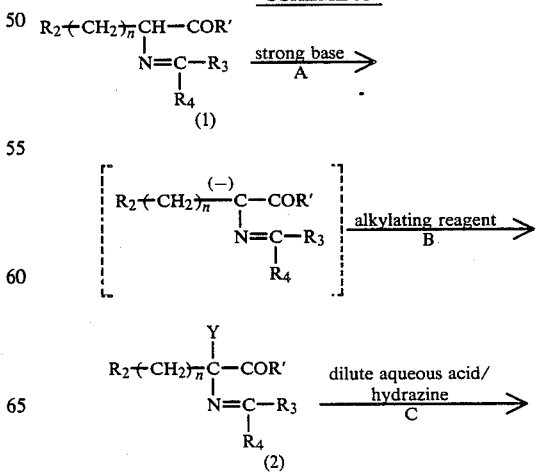

-continued
SCHEME A

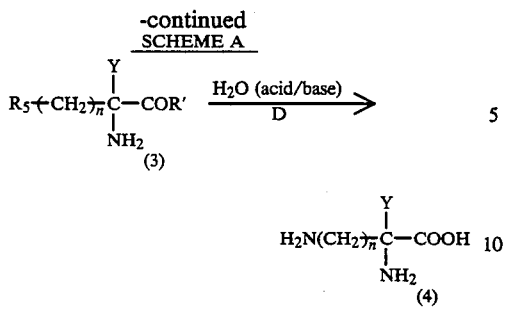

In the above reaction sequence, n is 3 or 4; R' is (C$_1$-C$_8$)alkoxy, for example, methoxy, ethoxy, isopropoxy, n-propoxy, or tert-butoxy; R$_3$ is hydrogen, phenyl, (C$_1$-C$_4$)alkyl, methoxy, or ethoxy; R$_4$ is phenyl or (C$_1$-C$_4$)alkyl; or R$_3$ and R$_4$ taken together may form an alkylene group of from 5 to 7 carbon atoms, that is, —CH$_2$—(CH$_2$)$_m$—CH$_2$— wherein m is an integer of from 3 to 5; R$_2$ is a group of the formula:

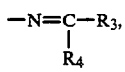

wherein R$_3$ and R$_4$ have the meanings defined above,

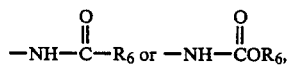

wherein R$_6$ is phenyl, benzyl, or (C$_1$-C$_4$)alkyl; R$_5$ is

wherein R$_6$ has the meaning defined above and Y is —CH$_2$F or —CH$_2$CL.

Suitable strong bases which may be employed in Step A of the above reaction sequence to form the carbanion intermediate are those which will abstract a proton from the carbon atom alpha to the carboxy group. Examples of strong bases are alkyl lithium, for example, butyl lithium or phenyl lithium; lithium di-alkylamide, for example, lithium diisopropylamide; lithium amide; potassium tert-butylate; sodium amide; metal hydrides, for example, sodium hydride or potassium hydride; tertiary amines, such as triethylamine; lithium acetylide or dilithium acetylide. Lithium acetylide, dilithium acetylide, sodium hydride, lithium diisopropylamide, and sodium tert-butylate are particularly preferred bases.

Alkylating reagents employed in Step B of the above reaction sequence have the formula X$_1$CH$_2$X wherein X$_1$ is fluorine or chlorine and X is chlorine, bromine, or iodine. The compounds of formula X$_1$Ch$_2$X are: chlorofluoromethane, bromofluoromethane, or iodofluoromethane (when Y is —CH$_2$F), dichloromethane, iodochloromethane, or bromochloromethane (when Y is —CH$_2$Cl). The alkylating reagents are known compounds.

The alkylation is carried out in a suitable aprotic solvent, such as dimethylsulfoxide, diemthylformamide, dimethylacetamide, benzene, toluene, or ethers, such as tetrahydrofuran, diethyl ether or dioxane.

The amino and carboxy protecting groups of compound (2) can be removed to afford compound (4) in one step by treatment with an aqueous acid, for example, hydrochloric acid or toluene sulfonic acid at a temperature of about 0° to 160° C. for about 4 to 24 hours. When the amino groups are protected as a Schiff's base, it is preferred, however, to remove the amino protecting groups first by treating compound (2) with a dilute aqueous acid, for example, hydrochloric acid or with hydrazine or phenylhydrazine in a solvent, such as a lower alcohol, for example, methanol or ethanol, an ether, a chlorinated hydrocarbon, benzene, or water. Removal of the carboxylic protecting group and the amino protecting groups, when the amine groups are protected other than as a Schiff's base can be accomplished by treatment of compound (3) with a concentrated aqueous acid, for example, hydrobromic acid at a temperature of about 0° to 160° C. or an aqueous base.

The amine and carboxy protected derivatives of formula (1), wherein R$_2$ is a group of the formula

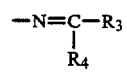

can be prepared, when R$_3$ is other than methoxy or ethoxy, by treating an ornithine ester or lysine ester with a suitable carbonyl compound using procedures known in the art generally for forming a Schiff's base. When R$_3$ is hydrogen, the appropriate amino acid ester can be treated with benzaldehyde or a (C$_1$-C$_9$)alkanal, for example, 1-propanal, 1-butanal, 2,2-dimethylpropan-1-al, or 2,2-diethylbutan-1-al, When R$_3$ is phenyl, the ornithine ester or lysine ester can be treated with benzophenone or a phenyl (C$_1$-C$_8$)alkyl ketone, for example, phenyl methyl ketone, phenyl ethyl ketone, phenyl isopropyl ketone, phenyl n-butyl ketone, or phenyl tert-butyl ketone. When R$_3$ is (C$_1$-C$_8$)alkyl, the ornithine ester or lysine ester can be treated with a phenyl (C$_1$-C$_8$)alkyl ketone, as described above, or with a di(C$_1$-C$_8$)alkyl ketone, for example, dimethyl ketone diethyl ketone, methyl isopropyl ketone, di-n-butyl ketone, or methyl tert-butyl ketone. The carbonyl compounds are known in the art, or may be prepared by procedures well known in the art.

When R$_3$ is methoxy or ethoxy, the ornithine ester or lysine ester can be treated with a benzoyl halide, for example, the chloride or a (C$_1$-C$_9$)alkanoic acid halide, for example, acetyl chloride, propionyl chloride, butyryl chloride, tert-butyryl chloride, 2,2-diethylbutyryl chloride, or valeryl chloride, at 0° C. in a solvent, such as an ether, methylenechloride, dimethylformamide, dimethylacetamide, or chlorobenzene, in the presence of an organic base, such as triethylamine or pyridine. The resulting amide derivative is then combined with an alkylating reagent, such as, when R$_3$ is methoxy, with methylflourosulfonate, dimethylsulfate, methyliodide, methyl-p-toluene-sulfonate, or trimethyloxonium hexafluorophosphate, or when R$_3$ is ethoxy, with triethyloxonium tetrafluoroborate at about 25° C. in a chlorinated hydrocarbon solvent, such as methylene chloride, chlorobenzene or chloroform. The reaction mixture is then refluxed for about 12 to 20 hours. The mixture is then cooled to about 25° C., an organic base such as triethylamine or pyridine is added, the solution is extracted with brine, and the product isolated by conventional procedures.

When in compound (1), R$_3$ and R$_4$ together form (C$_5$-C$_7$)alkylene, the protected amino acid ester obtained by treating the amino acid ester with a cyclic alkanone selected from cyclopentanone, cyclohexanone, and cycloheptanone to form a Schiff's base by procedures generally known in the art.

When $R_2$ is

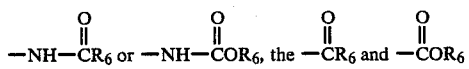

protecting groups are introduced by the following process: The α-amino group of ornithine or lysine is protected by treating ornithine or lysine with an excess of a copper salt, for example, copper carbonate, in boiling water for about 1 to 6 hours. Upon cooling to room temperature, the mixture is filtered and the filtrate containing the copper complex is treated with an appropriate acid halide, when $R_2$ is

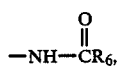

or an appropriate alkyl or aryl haloformate, when $R_2$ is

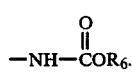

The acylation reaction is carried out in an inert solent, for example, acetone, in the presence of a base, such as sodium bicarbonate or sodium hydroxide. Treatment with hydrogen sulfide then destroys the copper complex. Illustrative acid halides which may be employed are acetyl chloride, propionyl chloride, benzoyl chloride, or 2-phenylacetyl chloride. Illustrative haloformates which may be employed are benzyl chloroformate, phenyl chloroformate, methyl chloroformate, or ethyl chloroformate.

The amino acid ester employed to prepare the compounds of formula (1) can be formed by known procedures. For example, the amino acid can be treated with an appropriate alcohol, such as methanol, ethanol, or n-butanol saturated with HCl gas or, when it is desired to prepare a tert-alkyl ester, with an appropriate ($C_1$–$C_8$)alkene in the presence of a strong acid.

The preparation of 2,5-diamino-2-fluoromethylpentanoic acid (Formula IIa) from ornithine methyl ester by fluoromethylation of methyl 2,5-bis(benzylideneamino)pentanoate and the deprotection of methyl 2-fluoromethyl-2,5-bis(benzylideneamino)pentanoate is described by P. Bey et al., *J. Org. Chem.*, 44, 2732 (1979), the disclosure of which is incorporated herein by reference. The aforesaid reference also describes the preparation of 2-chloromethyl-2,6-diaminohexanoic acid (Formula VIIb) from methyl 2,6-bis(benzylideneamino)hexanoate and of 2-chloromethyl-2,5-diaminopentanoic acid (Formula VIIa) from 3-amino-3-(hydroxymethyl)-2-piperidone. The preparation of 2,5-diamino-2-chloromethylpentanoic acid (formula VIIIa) from methyl 2,5-bix(benzylideneamino)pentanoate is described by B. Metcalf et al., *J. Am. Chem. Soc.*, 100, 2551 (1978).

The compound of Formula IV, which is 5-guanidinopropyl-2-amino-2-fluontanoic acid, can be prepared by treatment of α-fluoromethylornithine with an alkylisothiouronium salt, for example, ethylisothiouronium hydrobromide by procedures generally known in the art [See *Organic Synthesis*, III, 440 (1955) and P. Bey et al., *J. Org. Chem.*, 44, 2732 (1979)]. The reaction is carried out in the presence of a base, for example, aqueous sodium hydroxide or potassium hydroxide at a pH of about 8-12 and at a temperature of about 0° to 100° C. for about 6 hours to 8 days after which the reaction mixture is neutralized with concentrated mineral acid, for example, hydrochloric acid and the product isolated.

The preparation of 2-fluoromethyl-2,5-diaminopentanoic acid (IIa) via 2-fluoromethyl-2-amino-5-methoxypentanenitrile or 2-fluoromethyl-2-amino-5-benzyloxypentanentrile, and of 2-fluoromethyl-2,6-diaminohexanoic acid (IIb) via 2-fluoromethyl-2-amino-6-benzyloxyhexanenitrile, is described in European Patent Application No. 0046710, published Mar. 3, 1982 (Merrell-Toraude et Compagnie). The aforesaid preparations are also set forth herein Examples 6, 7, and 9.

The compounds of Formula IIIa or b, IVa or b, Va or b, and VIa or b, which are ester and/or N-acyl derivatives of 2-fluoromethyl-2,5-diamino-pentanoic acid (IIa) or 2-fluoromethyl-2,6-diaminohexanoic acid (IIb), can be prepared by methods generally known in the art from 2-fluoromethyl-2,5-diaminopentanoic acid (IIa) or 2-fluoromethyl-2,6-diaminohexanoic acid (IIb). It will be appreciated that, because 2-fluoromethyl-2,5-diaminopentanoic acid and 2-fluoromethyl-2,6-diaminohexanoic acid contain three potentially reactive functions (i.e. the α-amino group, the side-chain amino group, and the carboxy group), one or two such groups may have to be protected during the formation of a particular derivative to prevent unwanted side reactions. Since, however, in these compounds, the α-amino group is less reactive than the side-chain amino group, the side-chain amino group can be selectively derivatized without protecting the α-amino group, depending upon the reaction conditions employed.

The protected derivatives used in the methods hereinafter described are the compounds of Formula XI, XII, XIII, and XIV set forth below:

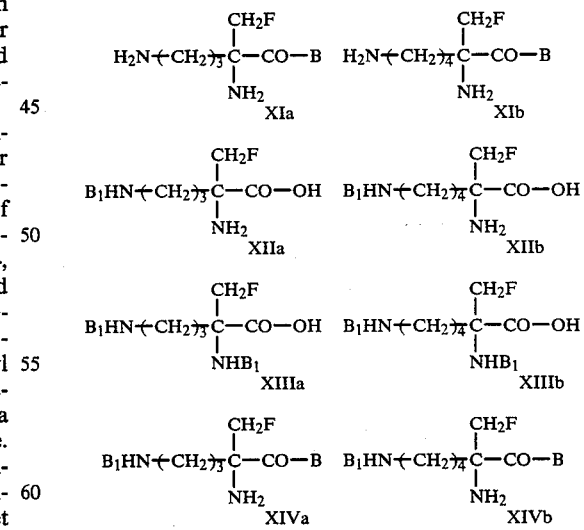

In Formula IXa or b and XIV a or b, B is tert-butoxy. In Formula XIIa or b, XIIIa or b, and XIVa or b, $B_1$ is benzyloxycarbonyl (Z) or tert-butyloxycarbonyl (Boc). Methods for employing the benzyloxycarbonyl group and the tert-butyloxycarbonyl group as protecting groups for the primary amino groups are known in the art. The benzyloxycarbonyl group, for example, can be introduced by treating an aqueous solution of the amino acid with benzylchloroformate in diethyl ether at pH 10–12 at 0° to 5° C. The tert-butyloxycarbonyl group can be introduced, for example, by reacting a solution of the amino acid in tetrahydrofuran/water with di-tert-butylcarbonate in the presence of triethylamine at room temperature. The benzyloxycarbonyl group can be removed, for example, by catalytic hydrogenation using Pd/C catalyst in ethanol at room temperature and atmosphere pressure. The tert-butyloxycarbonyl group can be removed by treatment with an acid, such as aqueous hydrochloric acid or aqueous trifluoroacetic acid, or hydrogen chloride in ethyl ether.

In general, the carboxy protected compounds of Formula IIIa or b can be prepared directly from the amino acids of Formula IIa or b using conventional esterification methods, such as: (a) treatment with an appropriate alcohol (R'—OH) saturated with hydrogen chloride using a reaction time of about 1 to 7 days at a temperature of about 25° C. to the boiling point of the alcohol employed, or (B) formation of the corresponding acid halide form the aimino acid, preferably the acid chloride, by treatment with thionyl chloride, followed by alcoholysis using the corresponding alcohol (R'—OH). Alternatively, in a preferred method, certain compounds of Formula IIIa or b can be prepared by (a) treating an amino-protected compound of Formula XIIa or b or XIIIa or b with an alkyl-halo compound of the formula R'—X and dicyclohexylamine in the presence of sodium iodide, when X is other than iodo, and (b) removing the protecting group(s) ($B_1$). In Formula R'—X, R' is ($C_1$–$C_8$)alkyl and X is chlorine, bromine, or iodine with the proviso that the alkyl group may not have a tertiary carbon atom present at the carbon-halogen bond. The esterification reaction is preferably performed in dimethylformamide at room temperature for 24 hours. The amino-protecting groups can be either benzyloxycarbonyl (B is Z) or tert-butyloxycarbonyl (B is Boc). Use of tert-butyloxycarbonyl is preferred since the deprotected product is obtained under acidic conditions.

When it is desired to prepare a compound of Formula IIIa or b wherein R' is a tert-alkoxy group, an amino-protected compound of Formula XIIa or b or Formula XIIIa or b, wherein $B_1$ is benzyloxycarbonyl, can be reacted with an appropriate tert-alkyl acetate and perchloric acid. The benzyloxycarbonyl group(s) can then be removed by catalytic hydrogenation under conditions that do not affect the tert-alkyl ester group. For example, the t-butyl ester of 2-fluoromethyl-2,5-diaminopentanoic acid (the carboxy-protected compound of Formula XIa) can be prepared from 5-N-benzyloxycarbonyl-2-fluoromethyl-2,5-diaminopentanoic acid by the reaction of t-butyl acetate and perchloric acid at room temperature followed by hydrogenation at 1 atmosphere with Pd/C in ethanol at room temperature.

The compounds of Formula IIIa or b wherein R' is methyl can be prepared conveniently by treating a compound of formula XIIIa or b wherein $B_1$ is tert-butyloxycarbonyl, with diazomethane followed by removal of the protecting group.

The ester compounds of Formula IIIa or b can also be obtained by deprotection of the appropriate ($C_1$–$C_8$)alkyl 2-(fluoromethyl or chloromethyl)-2,5-bis(benzylideneamino)pentanoate or a 2-(fluoro-methyl or chloromethyl)-2,6-bis(benzylideneamino)-hexanoate under mild conditions whereby the benzylidene groups are selectively removed. This can be accomplished using mild acidic conditions [1N hydrochloric acid, room temperature, as described by P. Bey et al., J. Org. Chem., 44, 2732 (1979) ] or using the reaction with hydrozine. The use of hydrazine is preferred for compounds having a tertiary-alkyl ester group, since the tert-alkyl ester function will undergo hydrolysis under acidic conditions.

The compounds of Formula IVa or b wherein $R_a'$ is $R_1CH(NH_2)CO$— wherein $R_1$ is hydrogen, ($C_1$–$C_4$)alkyl, benzyl, or p-hydroxybenzyl, can be made from a compound of Formula XIa or b, using methods conventional in the art for forming a peptide bond. For example, in one method a compound of Formula XIa or b can be reacted with an amino-protected amino acid of the formula $R_1CH(NHB_1)CO_2H$, wherein $R_1$ is as hereinbefore defined and B is benzyloxycarbonyl or tert-butyloxycarbonyl in the presence is carried out in an inert solvent, such as an ether (e.g. tetrahydrofuran, dimethoxyethane, or dioxane), methylene chloride, or chloroform at a temperature of about 0° to 35° C. for about 1 to 12 hours. Suitable coupling agents, such as dicyclohexylcarbodiimide are known in the art. After formation of the desired amino-protected peptide ester, the amino-protecting group is removed, and the ester function is hydrolyzed to give the desired compound of Formula IVa or b. When $B_1$ is benzyloxycarbonyl, the protecting group ($B_1$) can be removed and the tert-butyl ester function can be hydrolyzed selectively. Thus, catalytic hydrogenation will remove the benzyloxycarbonyl group ($B_1$), while acid hydrolysis will cleave the tert-butyl ester function. The amino-deprotection reaction and the ester hydrolysis can be accomplished in any order. When $B_1$ is tert-butoxycarbonyl, the amino-protecting group can be removed and the tert-butyl ester function can be hydrolyzed in one step by reaction with an acid.

An alternative and preferred method for preparing a compound of Formula IVa or b, wherein $R_a'$ is $R_1CH(NH_2)CO$— wherein $R_1$ is as hereinbefore described, involves the reaction of a compound of Formula XIa or b with an activated derivative of the amino acid such as the N-hydroxy-succinimide ester of the formula:

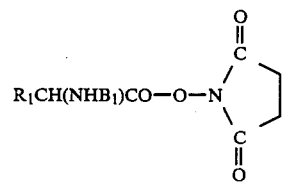

XV wherein $R_1$ is as hereinbefore described and $B_1$ is benzyloxycarbonyl or t-butyloxycarbonyl. The coupling reaction housing the N-hydroxysuccinimide ester is preferably carried out, for example, at room temperature in dimethyoxyethane with N-methyl morpholine added to the reaction mixture.

The compounds of Formula IVa or b, wherein $R_a'$ is ($C_1$–$C_4$)alkylcarbonyl can be prepared by reaction of a compound of formula Iia or b with an appropriate acid chloride or acid bromide, or an appropriate acid anhydride, in water in the presence of a base, such as sodium hydroxide or sodium boroate, at a temperature of about 0° to 25° C. and a reaction time of about ½ hour to 6 hours.

During the acylation of the side-chain amino group in the preparation of a compound of Formula IVa or b, wherein $R_a'$ is either $R_1CH(NH_2)CO-$ or $(C_1-C_4)$alkylcarbonyl, it is usually not necessary to protect the α-amino group of the compound of Formula XIa or b. If desired, however, the α-amino group may be protected and the protecting group can be subsequently removed.

The compounds of Formula Va or b wherein $R_a'$ is $(C_1-C_4)$alkylcarbonyl can be prepared from the corresponding compound of Formula IVa or b by employing the esterification procedures hereinbefore discussed. In particular, a compound of Formula IVa or b can be esterified by reaction with a suitable alkylhalo compound (R'—X) and dicyclohexylamine in the presence of NaI, when X is other than iodo. If desired, the α-amino group of the compound of Formula IVa or b can be protected during the esterification process and the protecting groups subsequently removed.

The compounds of Formula Va or b, wherein $R_a'$ is $R_1CH(NH_2)CO-$, wherein $R_1$ is as defined hereinbefore, can be prepared from a compound of the formula:

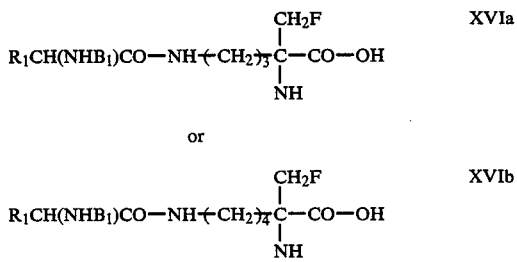

wherein $R_1$ is as defined hereinbefore and $B_1$ is benzyloxycarbonyl or tert-butyloxycarbonyl, by employing the esterification procedures hereinbefore discussed. When R' is tert-alkoxy, the protecting group $(B_1)$ must be benzyloxycarbonyl which can be removed by catalytic hydrogenation without affecting the tert-alkyl ester function.

If desired, the unprotected α-amino group of the compounds of Formula IVa or b or XVIa or b can be protected and the protecting groups can be subsequently removed.

The compounds of Formula VIa or b can be prepared from the compounds of Formula XIIa or b, wherein $B_1$ is tert-butyloxycarbonyl, by reaction with an appropriate acid chloride or bromide in anhydrous tetrahydrofuran or dioxane at reflux temperature in the presence of triethylamine followed by removal of the protecting group by reaction with an acid.

The compound of Formula VIIIa or b, which are the $(C_1-C_8)$alkyl esters of 2-chloromethyl-2,5-diaminopentanoic acid, or 2-chloromethyl-2,6-diaminohexanoic acid, can be made by conventional esterification procedures, such as described hereinbefore with respect to preparation of the compounds of Formula IIIa or b.

The compounds of Formula X, which are the corresponding lactams of 2-(fluoromethyl or chloromethyl)-2,5-diaminopentanoic acid, when n is 3, and of 2-(fluoromethyl or chloromethyl)-2,6-diaminohexanoic acid, when n is 4, can be made by methods that are conventional in the art for lactam formation. The compounds of Formula X can be made, for example, by treating the corresponding ester of Formula IIIa or b with a base (such as sodium hydroxide, potassium hydroxide, lithium hydroxide, sodium carbonate, potassium carbonate, sodium methoxide, potassium tert-butoxide, sodium amide, or an organic amine, e.g. trialkylamine, such as triethylamine) in a solvent (such as a lower alkanol, e.g. methanol, ethanol, isopropyl alcohol, n-butanol, water, dimethylformamide, dimethylsulfoxide, hexamethylphosphoramide) using a temperature of 0° to 120° C. and a reaction time of ½ hour to 24 hours, optimally under a nitrogen atmosphere.

In the process shown hereinbefore in SCHEME A, the ester compound (3) obtained in Step C can be converted, if desired, to the corresponding lactam (Formula X) which is then hydrolyzed to give the desired product (4). The lactams of Formula X can be hydrolyzed to the corresponding amino acids by methods generally known in the art. For example, the lactams can be treated with 6N hydrochloric acid at reflux temperature for 24 hours.

It will be apparent to those skilled in the art that the compounds of Formula I contain at least one chiral center, and that, therefore, the compounds can exist as optical isomers. The compounds of Formula I include the biologically active individual optical isomers of the compounds, or a mixture of the isomers, such as the racemates. Methods for resolving the racemates are well known in the art. For example, a racemic lactam of Formula X can be resolved using a (+)- or (−)-binaphthylphosphoric acid salt by the method of R. Viterbo et al., *Tetrahedron Letters*, 48, 4617 (1971). Other resolving agents may be employed, for example, (+)-camphor-10-sulfonic acid. The individual enantiomers of 2-fluoromethyl-2-amino-5-guanidinopentanoic acid can be prepared from the resolved ornithine analogs.

As pharmaceutical agents, the compounds of Formula I can be administered in various manners to achieve the desired effect. The compounds can be administered alone, in combination with each other, or in combination with pharmaceutically acceptable carriers or diluents, the proportion and nature of which are determined by the solubility and chemical properties of the compound selected, the chosen route of administration, and standard pharmaceutical practice. The compounds of Formula I may be administered orally in solid dosage forms, e.g. capsules, tablets, powders, or in liquid forms, e.g. solutions or suspensions. The compounds may also be injected parenterally in the form of sterile solutions or suspensions. Solid oral forms may contain conventional excipients, for instance: lactose, succrose, magnesium stearate, resins, and like materials. Liquid oral forms may contain various flavoring, coloring, preserving, stabilizing, solubilizing, or suspending agents. Parenteral preparations are sterile aqueous or nonaqueous solutions or suspensions which may contain various preserving, stabilizing, buffering, solubilizing, or suspending agents. If desired, additives, such as saline or glucose, may be added to make the solutions isotonic.

The amount of active compound administered will vary and can be any effective amount. Depending on the patient to be treated, the condition being treated, the mode of administration, and the particular compound employed, the effective amount of compound administered will vary from about 0.1 mg/kg to 500 mg/kg of body weight of the patient per unit dose and preferably will be about 10 mg/kg to about 100 mg/kg of body weight of the patient per unit dose. For example, a typical unit dosage form may be a table containing from 10 to 300 mg of a compound of Formula I which may be administered to the patient being treated 1 to 4 times daily to achieve the desired effect.

As used herein, the term "patient" is taken to mean warm blooded animals such as mammals, for example cats, dogs, rats, mice, guinea pigs, horses, bovine cows, sheep, and humans.

The term "unit dosage form " is used herein to mean a single or multiple dose form containing a quantity of the active ingredient and the diluent or carrier, said quantity being such that one or more predetermined unit are normally required for a single therapeutic administration. In the case of multiple dose forms, such as liquids or scored tablets, said predetermined unit will be one fraction such as 5 ml (teaspoon) quantity of a liquid or a half or quarter of a scored tablet, of the multiple dose form.

The invention also provides pharmaceutical formulations in which form the active compounds of the invention will normally be utilized. Such formulations are prepared in a manner well known in the pharmaceutical art and usually comprise at least one active compound of the invention and a pharmaceutically acceptable carrier or diluent therefor. A carrier or diluent may be solid, semisolid, or liquid material which serves as a vehicle, excipient, or medium for the active ingredient. Suitable diluents or carriers are well known. The pharmaceutical formulations may be adapted for enteral or parenteral use and may be administered to the patient in the form of tablets, capsules, suppositories, solutions, suspensions, or the like.

Illustrative examples for preparing the compounds of the invention and for demonstrating the pharmacological uses therefor, are given in the following examples.

EXAMPLE 1

Methyl 2-chloromethyl-2,6-diaminohexanoate

A. Methyl 2,6-bis(benzylideneamino)hexanoate

A suspension of 2,6-diaminohexanoic acid hydrochloride (18.26 g, 100 mmol) in dry methanol (100 ml) is saturated with gaseous hydrochloric acid and heated under reflux for 2 hours. Upon cooling, methyl 2,5-diaminhexanoate dihydrochloride crystallizes. To an ice cooled suspension of methyl 2,6-diaminohexanoate dihydrochloride (4.66 g, 20 mmol) in methylene chloride (50 ml) is added benzaldehyde (4.04 g, 40 mmol) and then dropwise a solution of triethylamine (4.24 g, 40 mmol) in methylene chloride (30 ml). The reaction mixture is allowed to stand overnight at room temperature under stirring and is then concentrated under reduced pressure to give a residue which is extracted into ether (diethyl ether). The ether extract is washed with water and brine, dried over $MgSO_4$, and concentrated to give methyl 2,6-bis(benzylideneamino)hexanoate as an oily residue.

B. Methyl 2-chloromethyl-2,6-(benzylideneamino)hexanoate

To a solution of lithium diisopropylamide (10 mmol) prepared in situ from a solution of 1N diisoproppylamine in tetrahydrofuran (THF) and a solution of butyl lithium (2N) in hexane and hexamethylphosphoramide (HMPA) (2.5 ml) in THF cooled to $-78°$ C., magnetically stirred, and kept under nitrogen, is added slowly a solution of methyl 2,6-bis(benzylideneamino)hexanoate (3.365 g, 10 mmol) in dry THF (20 ml). The reaction mixture is stirred at $-78°$ C. for ½ hour, and then a solution of chlorobromoethane (1.3 g, about 10 mmol) in dry THF (10 ml) is added rapidly. the temperature is allowed to rise slowly to room temperature, and the stirring is continued overnight. The reaction mixture is quenched with water and extracted with ether. The ether extract is washed with water and concentrated at reduced pressure to give methyl 2-chloromethyl-2,6-bis(benzylideneamino)hexanoate as an oily residue.

C. Methyl 2-chloromethyl-2,6-diaminohexanoate

To a solution of methyl 2-chloromethyl-2,6-bis(benzylideneamino)hexanoate (2.85 g, 7.4 mmol) in ether (6 ml), is added 1N HCl (20 ml) under vigorous stirring. The reaction mixture is stirred overnight at room temperature and then extracted with ether. The aqueous phase is evaporated to dryness under vacuo to afford methyl 2-chloromethyl-2,6-diaminohexanoate dihydrochloride as an oily and hygroscopic residue (2.05 g).

NMR ($D_2O$): 4.05 (2H, q)—CH Cl; 3.87 (3H, s) —$CO_2Me$; 3.03 (2H, broad t, J=7 Hz) $H_2N$—$CH_2$—.

EXAMPLE 2

2-Chloromethyl-2,6-diaminohexanoic acid (monochlorohydrate)

A solution of methyl 2-chloromethyl-2,6-diaminohexanoate dihydrochloride (2.05 g, 7.3 mmol) in concentrated hydrochloric acid (HCl) (10 ml) is heated under reflux for 18 hours. Concentration under vacuo followed by treatment with charcoal affords an oily residue (2.1 g) which is dissolved in dry methanol. Upon addition of propylene oxide until pH 3–4, 2-chloromethyl-2,5-diaminohexanoic acid monochlorohydrate precipitates (1.25 g). Recrystallization from water/ethanol affords analytically pure 2-chloromethyl-2,6-diaminohexanoic acid monochlorohydrate as white crystals: m.p. 216 (dec).

EXAMPLE 3

2-Chloromethyl-2,5-diaminopentanoic acid

A. 3-Hydroxymethyl-3-amino-2-piperidone

2-Hydroxymethyl-2,5-diaminopentanoic acid hydrochloride (5 g or $2.5 \times 10^{-2}$ mol) is suspended in 75 ml of absolute methanol and the solution is saturated with dry hydrogen chloride. The homogenous solution is then heated under reflux for 48 hours. The reaction mixture is regularly saturated with dry hydrogen chloride. The solvent is evaporated under reduced pressure and the hygroscopic residue is dried under high vacuo (6.2 g) to give methyl 2-hydroxymethyl-2,5-diaminopentanoate dihydrochloride. The ester (6.2 g) is dissolved in 100 ml of absolute methanol, and 175 ml of a methanolic solution of sodium methylate (1.15 g of Na or $5 \times 10^{-2}$ mol) is added. The reaction mixture is stirred at room temperature under nitrogen for 24 hours. The solvent is evaporated under reduced pressure and the residue is extracted many times with hot chloroform to yield analytically pure 3-hydroxymethyl-3-amino-2-piperidone (2.9 g): m.p. 145° C.

B. 2-Chloromethyl-2,5-diaminopentanoic acid

3-Hydroxymethyl-3-amino-2-piperidone (2.8 g or $1.94 \times 10^{-2}$ mol) is added to a solution of thionyl chloride (1.4 ml or 1.94 or 1.94 x 10⁻1 mol) in anhydrous dimethyl formamide (20 ml). The reaction mixture is stirred at 80° C. under nitrogen for 24 hours. Thionyl chloride (1.4 ml or $1.94 \times 10^{-2}$ mol) is then added and the stirring is continued for 2 hours. The solvent is removed under reduced pressure. The residue is dried under high vacuo overnight, dissolved in 6N HCl (50 ml), and heated under reflux for 2 hours. The residue obtained after evaporation of the solvent is dissolved in absolute ethanol (100 ml) and is treated with charcoal. After filtration, the final volume of the filtrate is adjusted to 250 ml with absolute ethanol and 19.5 ml of a solution of triethylamine 1N in absolute ethanol is added. A mixture of 2-hydroxymethyl-2,5-diaminopentanoic acid and 2-chloromethyl-2,5-diaminopentanoic acid hydrochloride precipitates and is filtered and washed with 100 ml of ethanol, 450 ml of chloroform and 250 ml of ether. The filtrate is allowed to stand at 4° C. for 24 hours whereupon 2-chloromethyl-2,5-diaminopentanoic acid hydrochloride crystallizes contaminated with a trace of 2-hydroxymethyl-2,5-diaminopentanoic acid hydrochloride. The mixture of 2-hydroxymethyl-2,5-diaminopentanoic acid hydrochloride and 2-chloromethyl-2,5-diaminopentanoic acid hydrochloride is redissolved in HCl and the same purification procedure is repeated three times. The three batches of crude 20-chloromethyl-2,5-diaminopentanoic acid hydrochloride (1.8 g) are collected and crystallized from water (3.5 ml) and ethanol (17.5 ml) to give 1.3 g of analytically pure 2-chloromethyl-2,5-diaminopentanoic acid hydrochloride: m.p. 140°–142° C.

EXAMPLE 4

3-Amino-3-chloromethyl-2-piperidone

To a solution of 3-hydroxymethyl-3-amino-2-piperidone (7 g or 0.049 mol) in anhydrous dimethylformamide (50 ml) is added one equivalent of thionyl chloride (3.6 ml). The reaction mixture is stirred at 80° C. under nitrogen. After 24 hours, another equivalent of thionyl chloride (3.6 ml) is added and stirring is continued for 2 hour. Then the solvent is stripped off under reduced pressure. Trituration of the semi-solid residue with chloroform (2×30 ml) leaves 2.1 g of crystalline analytically pure 3-amino-3-chloromethyl-2-piperidone hydrochloride: m.p. 230° C.

EXAMPLE 5

2-Fluoromethyl-2,5-diaminopentanoate

A. Methyl 2-fluoromethyl-2,5-bis(benzylideneamino)pentanoate

To sodium hydride (10 mmol), washed with pentane, is added under nitrogen methyl 2,5-bis(benzylideneamino)pentanoate (3.22 g, 10 mmol) in HMPA (20 ml). After stirring the mixture for 4 hours at room temperature, the nitrogen inlet is disconnected and replaced by an expandable balloon. Then a solution of chlorofluoromethane (2.8 g, 40 mmol) in THF (20 ml) cooled to −50° C. is added. After stirring the solution for 2 hours at room temperature, the solvent is removed under reduced pressure and the residue is taken up with water and extracted with ether. The organic layer is washed with water and brine, dried over MgSO$_4$ and concentrated in vacuo to give 3.22 g of methyl 2-fluoromethyl-2,5-bis(benzylideneamino)pentanoate as an oil.

NMR (CDCl$_3$): δ 1.50–2.30 (m, 4, —CH$_2$CH$_2$—), 3.58 (m, 2, —CH$_2$N), 3.68 (s, 3, —CO$_2$CH$_3$), 4.67 (d, 2, $J_{HF}$=47 Hz, —CH$_2$F), 7.06–7.78 (m, 10, C$_6$H$_5$), 8.16 (s, 1, —CH═N—), 8.27 (s, 1, —CH═N—).

B. Methyl 2-fluoromethyl-2,5-diaminopentanoate

A mixture of methyl 2-fluoromethyl-2,5-bis(benzylideneamino)pentanoate (3.11 g) in diethyl ether (20 ml) and N aqueous HCl (100 ml) is stirred at room temperature for 3 hours. The aqueous phase is decanted, washed with ether, and concentrated in vacuo to give 2.5 g of methyl 2-fluoromethyl-2,5-diaminopentanoate dihydrochloride.

NMR (D$_2$O): δ 1.12–2.02 (m, 4, —CH$_2$]$_l$ $_{CH2}$—), 2.67 (m, 2, —CH$_2$N<), 3.49 (s, 3, —OCH$_3$), 4.48 (2q, ABX system, $J_{HH}$=10.5 Hz, $v_{HH}$=10 Hz, $J_{HF}$=47 Hz, 2, —CH$_2$]$_l$ $_F$).

C. 3-Amino-3-fluoromethyl-2-piperidone

To a solution of methyl 2-fluoromethyl-2,5-diaminopentanoate dihydrochloride (2.5 g) in methanol (30 ml) is added under nitrogen a solution of sodium methylate (prepared from 0.46 g of sodium in methanol (20 ml). The reaction mixture is stirred for 1 hour at room temperature and then concentrated in vacuo. The residue is taken up in CH$_2$Cl$_2$. The insoluble material is removed by filtration, and the filtrate is concentrated to give 1 g of 3-amino-3-fluoromethyl-2-piperidone: m.p. 132° C. (from CH$_2$CL$_2$/pentane).

NMR (CDCl$_3$): δ 1.5–2.4 (m, 6, —CH$_2$ and NH$_2$), 3.2–3.6 (m, 2, —CH$_2$N—), 4.32 (2 q, ABX system, 2, $J_{HH}$=22.5 Hz, $J_{HF}$=47 Hz, —CH$_2$F), 6.95 (s, 1, CONH).

D. 2-Fluoromethyl-2,5-diaminopentanoic acid

A solution of 3-amino-3-fluoromethyl-2-piperidone (1 g) in 6N aqueous HCl (20 ml) is heated at reflux for 24 hours. The residue obtained after concentration in vacuo is dissolved in ethanol (20 ml). The pH of the solution is adjusted to 3.5–4 by addition of triethylamine. Concentration under reduced pressure leaves a residue which is washed many times with hot chloroform. The insoluble material is recrystallized from H$_2$O/EtOH to yield 0.720 g of 2-fluoromethyl-2,5-diaminopentanoic acid hydrochloride monohydrate: m.p. >260° C.

NMR (D$_2$O): δ 1.6–2.2 (m 4, —CH$_2$—), 2.9–3.2 (m, 2, —CH$_2$N—), 4.68 (2q, ABX system, 2, $J_{HH}$=10 Hz, $_{HH}$=8.5 Hz, $J_{HF}$=47 Hz, —CH$_2$F).

EXAMPLE 6

2-Fluoromethyl-2,5-diaminopentanoic acid

A. 2-Fluoromethyl-2-amino-5-methoxypentanenitrile

Under an atmosphere of nitrogen, 3-methoxypropyl magnesium chloride is prepared from 3-methoxy-1-chloropropane (5.43 g, 50 mmol), prepared according to Haworth and Perking, *Chem. Zentralblatt*, II, 1271 (1912) and magnesium turnings (1.22 g, 50 mmol) in dry THF (50 ml). The mixture is heated under reflux for 3 hours, then cooled to −30° C. and a solution of fluoroacetonitrile (2.95 g, 50 mmol) in THF (30 mol) is added during 20 minutes. After keeping the mixture at −30° C. for ½ hour more, a solution of sodium cyanide (4.9 g, 100 mmol) and ammonium chloride (8.09 g, 150 mmol) in water (100 ml), previously cooled to 0° C., is added and the mixture is stirred for ¾ hour at room temperature. After saturating with sodium chloride, the THF layer is separated and the aqueous phase is extracted twice with ether. After drying (Na$_2$SO$_4$), the combined organic extracts are evaporated to give 2- fluoromethyl-2-amino-5-methoxypentanenitrile (4.0 g) as a brown oil.

NMR (CDCl$_3$): δ 1.77 (4H, m), 2.10 (broad s, NH$_2$), 3.30 (3H, s), 3.40 (2H, t), 4.32 (2H, ABX, J$_{AB}$=9 Hz, J$_{AX}$=J$_{BX}$=J$_{H-F}$=47 Hz).

B. 2-Fluoromethyl-2-phthalimido-5-methoxypentanenitrile

To a solution of 2-fluoromethyl-2-amino-5-methoxypentanenitrile (1.62 g, 10 mmol) and triethylamine (2.02 g, 20 mmol) in methylene chloride (30 ml), cooled to −20° C., is added phthaloyldichloride (2.03 g, 10 mmol) in methylene chloride (10 ml). The mixture is allowed to warm up to room temperature overnight. After washing with water, 1N HCl, water again, and drying (Na$_2$SO$_4$), the solvent is removed under reduced pressure to give 2.4 g of crude material. This is purified by chromatography on silica (ethyl acetate/petroleum ether 3:7).

NMR (CDCl$_3$): δ 2.15 (4H, m), 3.23 (3H, s), 3.40 (2H, t, J=6 Hz), 5.02 (2H, ABX, J$_{AB}$=9 Hz, J$_{AX}$=J$_{BX}$=J$_{H-F}$=46 Hz), 7.77 (4H, s).

C. 2-Fluoromethyl-2-phthalimido-5-iodopentanenitrile

2-Fluoromethyl-2-phthalimido-5-methoxypentanenitrile (1.20 g, 4.14 mmol), trimethylsilyl iodide (3.2 g, 16 mmol), and chloroform (15 ml) are heated to 60° C. under nitrogen for 48 hours. After removal of the solvent, the residue is dissolved in chloroform, washed with water, sodium thiosulfate solution, and water again, dried and evaporated to give the crude product as an oil (1.2 g). This is purified by chromatography on silica (ethyl acetate/petroleum ether 1:3) to give pure 2-fluoromethyl-2-phthalimido-5-iodopentanentrile NMR (CDCl$_3$): δ 2.0 (4H, m), 3.10 (2H, t), 4.90 (2H, ABX, J$_{AB}$=9 Hz, J$_{AX}$=J$_{BX}$=J$_{H-F}$=66 Hz), 7.70 (4H, s).

D. 2-Fluoromethyl-2,5-diphthalimidopentanenitrile

2-Fluoromethyl-2-phthalimido-5-iodopentanenitrile (1.20 g, 3.11 mmol) and potassium phthalimide (0.75 g, 4 mmol) are heated in dimethylformamide (25 ml) to 80° C. for 2 hours. After standing overnight at room temperature, the DMF is removed by vacuum distillation and the residue is dissolved in chloroform and washed with 1N KOH and water. After drying (Na$_2$SO$_4$), evaporation gives 2-fluoromethyl-2,5-dinaphthalimidopentanenitrile as a solid.

NMR (CDCl$_3$): δ 2.17 (4H, m), 3.73 (2H, t), 4.93 (2H, ABX, J$_{AB}$=9 Hz, J$_{AX}$=J$_{BX}$=J$_{H-F}$=46 Hz), 7.73 (8H, broadened s).

E. 2-Fluoromethyl-2,5-diaminopentanoic acid

2-Fluoromethyl-2,5-diphthalimidopentanenitrile (1.21 g, 3 mmol) is refluxed with concentrated hydrochloric acid (20 ml) for 4 days. After standing at room temperature for several hours. phthalic acid is removed by filtration, the filtrate is evaporated, the residue dissolved in 2N HCl (20 ml) and carefully extracted with ether (5×10 ml). After evaporation, the residue is dried carefully under vacuum (oil pump) overnight. It is dissolved in dry ethanol (7 ml) and, after filtration, propylene oxide (0.3 g, 5 mmol) in ethanol (1 ml) is added to precipitate the monohydrochloride. this is collected after standing overnight at room temperature and recrystallized from water/ethanol to give pure 20fluoromethyl-2,5-diaminopentanoic acid, monohydrochloride, m.p. 260° C. (dec); TLC (EtOH/NH$_4$OH 80/20):0.18.

NMR (D$_2$O): δ 1.93 (4H, m), 3.10 (2H, broad t), 4.83 (2H, ABX, J$_{AB}$=10 Hz, J$_{AX}$=J$_{BX}$=J$_{H-F}$=46 Hz).

EXAMPLE 71

2-Fluoromethyl-2,5-diaminopentanoic acid

A. 1-Chloro-e-benzyloxypropane

In a 2 l flask, a mixture of 3-chloropropanol (56.7 g), benzyl bromide (102.6 g) and dry THF (600 ml) is stirred and cooled with ice/salt mixture. Potassium tert-butoxide (70 g) is added in portions (5-10 g), maintaining the internal temperature at about 0° C. After the mixture is stirred for 3 more hours at room temperature, the solvent is evaporated. Addition of 1N HCl (1 l), extraction with ether (1 l), and evaporation of solvent gives crude material (113.6 g), which is distilled under vacuum to give 1-chloro-3- benzyloxypropane (108.4 g) b.p.$_{0.01}$ 60°-80° C.

NMR (CDCl$_3$): δ 1.97 (2H, q, J=6 Hz), 3.50 and 3.55 (4H, 2t, J=7 Hz), 4.41 (2H, s), 7.24 (5H, s).

B. 2-Fluoromethyl-2-amino-5-benzylxypentanenitrile

To magnesium turnings (30.6 g, 1.26 mol), suspended in dry ether (150 ml) is added methyl iodide (~0.5 ml) and then a solution of 1-chloro-3-benzyloxypropane (116 g, 0.63 mol) in ether (1.1 l0 at such a rate that gentle reflux is maintained. This procedure is performed under nitrogen. After the mixture is heated for 1 more hour under reflux, titration indicates Grignard formation to be complete. The solution is separated from the excess of magnesium (glass wool), transferred to a 6 l flask and, again under nitrogen, cooled to −40° C. Fluoroacetonitrile (33.48 g, 0.57 mmol) in ether (300 ml) is added slowly. The mixture is then kept at −40° C. for another ½ hour and is poured into a mixture of sodium cyanide (123 g), ammonium chloride (186 g), ice (600 g), and water (650 ml). The mixture is stirred vigorously and allowed to warm up to room temperature during 1 hour. Ether is added, the aqueous phase is saturated with sodium chloride, and the organic layer is separated. The aminonitrile is extracted with 1N HCl (2×750 ml) and re-extracted with ether (2×750 ml) after basification with concentrated ammonia. Drying (Na$_2$SO$_4$) and evaporation gives 2-fluoromethyl-2-amino-5-benzyloxypentanenitrile as a brown oil (74.8 g).

NMR (CDCl$_3$): δ 1.38-2.43 (4H, m), 3.45 (2H, m), 4.28 (2H, ABX, J$_{AB}$=9 Hz, J$_{AX}$=J$_{BX}$=J$_{H-F}$=47 Hz), 4.47 (2H, s), 7.30 (5H, s).

The product can be used for the next step without further purification.

C. 2-Fluoromethyl-2-phthalimido-5-benzyloxypentanenitrile

To a stirred solution of 2-fluoromethyl-2-amino-5-benzyloxypentanenitrile (74.8 g), triethylamine (100 g), and dry dichloromethane (450 ml), cooled in an ice bath, a solution of phthaloyldichloride (58 g) in dichloromethane (300 ml) is added slowly. Stirring is continued at room temperature overnight. The mixture is extracted with 2N HCl (2×750 ml), washed with water (2×750 ml), dried carefully (Na$_2$SO$_4$), evaporated to give a brown oil which, according to NMR analysis, contains some iso-phthalimide. The oil is dissolved in dry dichloromethane (500 ml), triethylamine (100 g) is added, and the mixture is refluxed for 3 hours. Work-up as described above gives an oil which is purified by flash-chromatography on silica (2 kg, petroleum ether-/ethyl acetate 4:1). Crystallization from ether gives 2-fluoromethyl-2-phthalimido-5-benzyloxypentanenitrile (49.4 g).

NMR (CDCl$_3$): δ 1.5–3.0 (4H, m), 3.52 (2H, t), 4.44 (2H, s), 5.03 (2H, ABX, $J_{AB}$=9 Hz, $J_{AX}$=$J_{BX}$=$J_{H-F}$=47 Hz), 7.30 (5H, s), 7.80 (4H, s).

In an improved procedure, the crude oil obtained after work-up is put on a column of florisil (750 g) and the column is eluted with diethyl ether. Upon concentration, the title compound crystallizes.

D.
2-Fluoromethyl-2-phthalimido-5-hydroxypentanenitrile

To a solution of 2-fluoromethyl-2-phthalimido-5-benzyloxypentanenitrile (49.4 g) in dry dichloromethane (400 ml) is added TMSI (45 ml, 2.2 equivalents, and the mixture is stirred at room temperature overnight. The solvent is removed under vacuum. The residue is evaporated two times more with dichloromethane and then dissolved in chloroform. After addition of triethylamine (60 ml), the mixture is refluxed for 3 hours. Washing with water, 1N HCl (2×), water again, drying, and evaporation gives 2-fluoromethyl-2-phthalimido-5-hydroxypentanenitrile as a brown oil (42.8 g).

NMR (CDCl$_3$): δ 1.0–2.9 (6H+OH, m), 3,65 (2H, t+additional splitting), 5.03 (2H, ABX, $J_{AB}$=9Hz, $J_{AX}$=$J_{BX}$=$J_{H-F}$=47 Hz), 7.80 (4H, s).

E.
2-Fluoromethyl-2-phthalimido-5-methanesulfonyloxypentanenitrile

A mixture of 2-fluoromethyl-2-phthalimido-5-hydroxypentanenitrile (42.8 g), dry pyridine (170 ml), and dry dichloromethane (350 ml) is stirred and cooled with ice/salt mixture. Freshly distilled methanesulfonylchloride (15.7 g) in dichloromethane (200 ml) is slowly added, and stirring is continued at room temperature overnight. The mixture is then poured onto ice/2N HCl, and the organic phase is extracted subsequently with 1N HCl, water, 10 % sodium bicarbonate, and water (3×). Drying (MgSO$_4$), treatment with charcoal (room temperature), and evaporation gives 2-fluoromethyl-2-phthalimido-5-methanesulfonyloxypentanenitrile as a brown oil (42 g).

NMR (CDCl$_3$): δ 1.1–2.9 (4H, m), 3.03 (3H, s), 4.31 (2H, t+additional splitting) 5.03 (2H, ABX, $J_{AB}$=9 Hz, $J_{AX}$=$J_{BX}$=$J_{H-F}$=47 Hz), 7.86 (4H, s).

F. 2-Fluoromethyl-2-phthalimido-5-iodopentanenitrile

A solution of 2-fluoromethyl-2-phthalimido-5-methanesulfonyloxypentanenitrile (42 g) and sodium iodide (35.7 g) in acetone (600 ml) is stirred and heated under reflux. After about ½ hour, the mixture solidifies. Acetone (500 ml) is added, and refluxing and stirring is continued overnight. The salts are removed by filtration and washed several times with acetone. The acetone is evaporated to give a residue which is dissolved in ether (1.5 l). The ether solution is washed subsequently with water (2×), sodium sulfite solution, and water again (3×). After drying (MgSO$_4$) and evaporating the ether, 2-fluoromethyl-2-phthalimido-5-iodopentanenitrile is obtained as an oil (34.1 g).

NMR (CDCl$_3$): δ 1.0–2.9 (4H, m), 3.16 (2H, t), 4.97 (2H, ABX, $J_{AB}$=9 Hz, $J_{AX}$=$J_{BX}$=$J_{H-F}$=47 Hz), 7.80 (4H, s).

G. 2-Fluoromethyl-2,5-diphthalimidopentanenitrile

A mixture of 2-fluoromethyl-2-phthalimido-5-iodopentanenitrile (34.1 g), potassium phthalimide (16.6 g), and dry DMF (230 ml) is stirred and heated at 70°–80° C. for 5 hours. The DMF is removed under reduced pressure, the residue is dissolved in chloroform, and the chloroform solution is washed with water (2×), 1N KOH (2×), 1N HCl, and water again (3×). The washed chloroform solution is dried and solvent is removed to give an oil which is evaporated twice with chloroform/ether to give a solid. Recrystallization from ether (500 ml) gives pure 2-fluoromethyl-2,5-diphthalimidopentanenitrile (18.5 g).

NMR (CDCl$_3$): δ 1.5–2.9 (4H, m), 3.78 (2H, t), 5.03 (2H, ABX, $J_{AB}$=9 Hz, $J_{AX}$=$J_{BX}$=$J_{H-F}$=47 Hz), 7.76 (8H, s).

H. 2-Fluoromethyl-2,5-diaminopentanoic acid

2-Fluoromethyl-2,5-diphthalimidopentanenitrile (18.5 g) is heated under reflux with concentrated HCl for 4 days. After the reaction mixture is cooled to room temperature, phthalic acid is removed by filtration,a and the filtrate is evaporated to dryness. The residue is dissolved in water, and the water solution is extracted twice with ether and then taken to dryness. Last traces of water and HCl are removed by evaporating the residue twice with isopropanol. The residue is dissolved in ethanol (300 ml), ammonium chloride is removed by filtration,a and propylene oxide (9.5 g) is added. The mixture is kept in the refrigerator overnight, and the crude monohydrochloride is collected by filtration. It is dissolved in the minimum amount of water, filtered (millipore)0, and recrystallized by addition of 5–10 volumes of ethanol to give 2-fluoromethyl-2,5-diaminopentanoic acid as the monohydrochloride, monohydrate (7.6 g).

Analysis for C$_6$H$_{13}$FN$_2$O$_2$, HCl, H$_2$O: Calculated: C, 32.96; H, 7.38; N, 12.81 %; Found : C, 33.08; H, 7.23; N, 13.13 %.

EXAMPLE 8

2-Fluoromethyl-2-phthalimido-5-iodopentanenitrile

In this example, 2-fluoromethyl-2-phthalimido-5-iodopentanenitrile is made directly from 2-fluoromethyl-2-phthalimido-5-benzyloxypentanenitrile fluoromethyl-2-phthalimido-5-benzyloxypentanenitrile as follows:

Chlorotrimethylsilyl (22 g) is added dropwise over 20 minutes to a suspension of NaI (30 g) in CH$_3$CN (300 ml) cooled to 0° C. Stirring is continued for 30 minutes at room temperature. 2-Fluoromethyl2-phthalimido-5-benzyloxypentanenitrile (25 g) in CH$_3$CN (50 ml) is added, and the mixture is stirred overnight at room temperature. This mixture is then poured into cold water containing sodium bicarbonate and sodium thiosulfate, and extracted with diethyl ether. The organic layer is dried over MgSO$_4$ and concentrated in vacuo. The residue is taken up in THF (200 l) and triethylamine (7 g) is added. After stirring for 1 hour, the mixture is poured into water and extracted with diethyl ether. The organic layer is washed with H$_2$O, dried over MgSO$_4$, and concentrated in vacuo. The residue, a mixture of 2-fluoromethyl-2-phthalimido-5-hydroxypentanenitrile and 2-fluoromethyl-2-phthalimido-5-iodopentanenitrile is taken up in CH$_3$CN (50 ml) and added to a solution of iodotrimethylsilyl prepared as described above from TMS Cl (22 g) and NaI (30 g) in CH₃CH (300 ml). The mixture is stirred overnight at room temperature. Then it is poured into cold water containing sodium bicarbonate and sodium thiosulfate, and extracted with diethyl ether. The residue obtained after concentration of the organic layer in vacuo is filtered on a florisil column (30 g). Elution with diethyl ether and removal of the solvent under reduced pressure gives 22 g of 2-fluoromethyl-2-phthalimido-5-iodopentanenitrile as an oil.

EXAMPLE 9

2-Fluoromethyl-2,5-diaminohexanoic acid

A. 4-Benzyloxybutanol

In a 2 l flask, a solution of 1,4-butanediol (45 g, 0.5 mol) and benzyl bromide (85.5 g, 0.5 mol) in dry THF (500 ml) is cooled to 0° C. (internal temperature). With vigorous stirring, potassium-tert-butoxide (56 g, 0.5 mol) is added in ~5 g portions, maintaining the internal temperature below 10° C. After addition of 1N HCl (2 l), the mixture is saturated with sodium chloride, extracted with ether (1.5 l), washed with water, dried, and finally evaporated to give an oil (88 g) which is distilled under vacuum to give pure 4-benzyloxybutanol (63.5 g), b.p.$_{0.2}$ 113°–114° C.

NMR (CDCl₃): δ 1.65 (4H, m), 2.9 (1H, s), 3.53 (4H, m), 4.50 (2H, s), 7.33 (5H, s).

B. 1-Chloro-4-benzyloxybutane

A mixture of 4-benzyloxybutanol (64.8 g, 0.36 mol) in dry pyridine (200 ml) is stirred and heated to 50°–60° C. A solution of thionyl chloride (43 g, 0.36 mol) in pyridine (100 ml) is added slowly, and the mixture is kept at 60° C. for one more hour. After cooling to room temperature, the reaction mixture is poured into a mixture of ice and 2N HCl. The mixture is saturated with sodium chloride, extracted with ether, and washed successively with water, 10% sodium bicarbonate, and water. Evaporation of solvent gives a yellow oil (49.7 g) which is distilled under vacuum to give pure 1-chloro-4-benzyloxybutane (47 g), b.p.$_{0.03-0.05}$ 85°–90° C.

NMR (CDCl₃): δ 1.83 (4H, m), 3.88 (4H, m), 4.53 (2H, s), 7.37 (5H, s).

C. 2-Fluoromethyl-2-amino-6-benzyloxyhexanenitrile

Under an atmosphere of nitrogen, the Grignard reagent is prepared from 1-chloro-4-benzyloxybutane (39.7 g, 0.2 mol), magnesium turnings (10 g, 0.4 mol), and dry ether (400 ml). The Grignard solution is separated from the excess of magnesium, transferred to a 2 l flask, and cooled to −40° C. A solution of fluoroacetonitrile (10.6 g, 0.18 mol) in ether (100 ml) is added slowly, the temperature being maintained between −40° and −30° C. Stirring is continued for 30 minutes more at this temperature. The reaction mixture is then poured into a vigorously stirred solution of sodium cyanide (39 g) and ammonium chloride (59 g) in water (200 ml) containing some ice (200 g). The mixture is vigorously stirred and allowed to warm up to room temperature during one hour. The organic phase is separated and extracted with 1N HCl (2×250 ml). Basification with concentrated ammonia, extraction with ether, drying, and evaporation gives 2-fluoromethyl-2-amino-6-benzyloxyhexanenitrile as a brown oil (28.3 g).

NMR (CDCl₃): δ 1.63 (6H +2 NH , M +broad s), 3.48 (2H, m), 4.27 (2H, ABX, $J_{AB}$=9 Hz, $J_{AX}$=$J_{BX}$=$J_{H-F}$=47 Hz), 4.48 (2H, s), 7.33 (5H, s).

The product can be used for the next step without further purification.

D. 2-Fuoromethyl-2-phthalimido-6-benzyloxyhexanenitrile

A solution of 2-fluormethyl-2-amino-6-benzyloxyhexanenitrile (28.3 g, 113 mmol) and triethylamine (34.4 g) in dry dichloromethane (200 ml) is cooled in an ice bath, and a solution of phthaloyl dichloride (20.7 g) in dichloromethane (100 ml) is added slowly. After stirring at room temperature overnight, the solution is washed with 2N HCl and with water. The solution is dried, treated with charcoal, and evaporated to give a brown oil (37 g). Flash chromatography on silica gel (1 kg, ether/petroleum ether 30:70) gives pure 2-fluoromethyl-2-phthalimido-6-benzyloxyhexanenitrile (16 g).

NMR (CDCl₃): δ 1.70 (6H, m), 3.47 (2H, broadened t), 4.47 (2H, s), 5.07 (2H, ABX, $J_{AB}$=9 Hz, $J_{AX}$=$J_{BX}$=$J_{H-F}$=47 Hz), 7.32 (5H, s), 7.87 (4H, s).

E. 2-Fluoromethyl-2-phthalimido-6-hydroxyhexanenitrile

A solution of 2-fluoromethyl-2-phthalimido-6-benzyloxyhexanenitrile (15.5 g, 40.8 mmol) and trimethylsilyliodide (13 ml, 2.2 equivalents) in dry dichloromethane (100 ml) is stirred at room temperature under nitrogen overnight. After removing the solvent under vacuum, the residue is dissolved in dry chloroform, triethylamine (17 ml, 3 equivalents) is added, and the mixture is refluxed for 30 minutes. Upon cooling, the solution is stirred with 2N HCl (250 ml) for 15 minutes, the phases are separated, and the organic layer is washed with sodium bicarbonate and with water. After evaporation, the residue is dissolved in THF and water (20 ml). Drops of 6N HCl are added, and the resulting mixture is stirred for several minutes. The solvent is removed by evaporation, and the residue obtained in dissolved in chloroform, washed with water, and dried. Removal of solvent gives the crude title compound as an oil (12 g). Chromatography on silica (300 g, eluant: ethylacetate) gives 2-fluoromethyl-2-phthalimido-6-hydroxyhexanenitrile (9.0 g).

NMR (CDCl₃): δ 1.25–2.0+2.0–3.0 (7H, 2m), 3.57 (2H, broadened t), 5.03 (2H, ABX, $J_{AB}$=9 Hz, $J_{AX}$=$J_{BS}$=$J_{H-F}$=46 Hz), 7.80 (4H, s).

F. 2-Fluoromethyl-2-phthalimido-6-methanesulfonyloxyhexanenitrile

A solution of 2-fluoromethyl-2-phthalimido-6-hydroxyhexanenitrile (9.0 g, 31 mmol) and pyridine (60 ml) in dry dichloromethane (150 ml) is cooled in an ice bath, and methanesulfonyl chloride (3.6 g, 31 mmol), diluted with a small amount of dichloromethane, is added slowly with efficient stirring. Stirring is continued at room temperature overnight. The reaction mixture is washed with 2N HCl and dried. Evaporation of solvent gives 2-fluoromethyl-2-phthalimido-6-methanesulfonyloxyhexanenitrile as a yellow oil (10.84 g).

NMR (CDCl₃): δ 1.83 (6H, m), 3.00 (3H, s), 4.23 (2H, broadened t), 5.00 (2H, ABX, $J_{AB}$=9Hz, $J_{AX}$=$J_{BX}$=$J_{H-F}$=46 Hz), 7.83 (4H, s).

G. 2-Fluoromethyl-2-phthalimido-6-iodohexanenitrile

2-Fluoromethyl-2-phthalimido-6-methanesulfonyloxyhexanenitrile (10.84 g, 29.5 mmol) and sodium iodide (8.8 g, 2 equivalents) are refluxed in acetone overnight. The reaction mixture is filtered and solvent is removed by evaporation. The residue obtained is dissolved in ether and washed with water, sodium bisulfite, and water again. Upon concentration, 2-fluoromethyl-2-phthalimido-6-iodoheanenitrile crystallizes (9.0 g).

NMR (CDCl$_3$): δ 1.4–2.6 (6H, m), 3.18 (2H, broadened t), 5.02 (2H, ABX, $J_{AB}=9$ Hz, $J_{AX}=J_{H\text{-}F}=46$ Hz), 7.86 (4H, s).

H. 2-Fluoromethyl-2,6-diphthalimidohexanenitrile

A mixture of 2-fluoromethyl-2-phthalimido-6-iodohexanenitrile (9.0 g, 22.5 mmol), dry DMF (30 ml), and potassium phthalimide (4.2 g, 1 equivalent) is stirred and heated at 80° C. for 4 hours. The DMF is removed under reduced pressure (0.1 mm Hg), and the residue is taken up in chloroform. The chloroform mixture is filtered and the filtrate is washed with 2N NaOH, 2N HCl, and water. Evaporation of solvent gives a residue which, when dissolved in the minimum amount of acetone, crystallizes upon addition of ether. After standing at 5° C. overnight, the colourless crystals of 2-fluoromethyl-2,6-diphthalimidohexanenitrile are collected (7.0 g), m.p. (Kofler) 136° C.

NMR (CDCl$_3$): δ 1.2–3.0 (6H, m), 3.70 (2H, broadened t), 5.07 (2H, ABX, $J_{AB}=9$ Hz, $J_{AX}=J_{BX}=J_{H\text{-}F}=46$ Hz), 7.77+7.83 (8H, 2s).

I. 2-Fluoromethyl-2,6-diaminohexanoic acid

2-Fluoromethyl-2,6-diphthalimidohexanenitrile (5.0 g, 11.9 mmol) is refluxed with concentrated HCl for 14 hours. After addition of more concentrated HCl, heating is continued for 18 hours more. After the reaction mixture is cooled to room temperature, phthalic acid is removed by filtration, and the filtrate is evaporated to dryness. The residue is dissolved in water, treated with charcoal, and extracted three times with ether. Solvent is removed by evaporation. The residue is dried carefully (oil pump) and dissolved in dry ethanol. Ammonium chloride is removed by filtration, and the filtrate is treated with an excess of propylene oxide. After 2 hours at room temperature, the precipitate is removed by filtration and washed with ethanol and ether to give crude material (2.6 g). This material is dissolved in the minimum amount of water. The water solution is filtered (membrane filter) and upon addition of ethanol to the filtrate, 2-fluoromethyl-2,6-diaminohexanoic acid crystallizes (1.0 g). A second crop (0.9 g) is obtained from the mother liquor. This second crop is recrystallized once more in the same manner. Total yield of pure compound as the monohydrochloride: 1.50 g, m.p. 212° C.

Analysis for C$_7$H$_{15}$FN$_2$O$_2$, HCl: Calculated : C, 39.17; H, 7.51; N, 13.05 %; Found : C, 39.33; H, 7.14; N, 13.04 %.

NMR (D$_2$O/DCl): δ 1.2–2.3 (6H, m), 3.09 (2H, broad t), 4.91 (2H, ABX, $J_{AB}=10$ Hz, $J_{AX}=J_{BX}=J_{H\text{-}F}=46$ Hz).

EXAMPLE 10

2-Fluoromethyl-2,5-diaminopentanoic acid (MFMO), 2-chloromethyl-2,5-diaminopentanoic acid (MCMO), 2-fluoromethyl-2,6-diaminohexanoic acid (DFML), and 2-chloromethyl-2,6-diaminohexanoic acid (MCML) were tested for inhibition of rat liver ornithine decarboxylase in vitro according to the procedure of B. Metcalf et al., *J. Am. Chem. Soc.*, 100, 255 (1978). The results obtained are set forth in TABLE I, below:

TABLE I

Kinetic constants of the time-dependent inhibition of rat liver ODC (in vitro)

| Compound | K$_I$ (μM) | T$_{\frac{1}{2}}$ (min) | t$_{\frac{1}{2}}$ (min) at 10 μM |
|---|---|---|---|
| MFMO | 75 | 1.6 | 14 |
| MCMO | no apparent saturation kinetics | | 22 |
| MFML | 430 | 2.0 | 88 |
| MCML | no apparent saturation kinetics | | 62 |

K$_I$ is the concentration of compound which gives half-maximal rate of inhibition.

T$_{\frac{1}{2}}$ (min) is the half-life of inhibition at infinite concentration of inhibitor.

t$_{\frac{1}{2}}$ (min) is the half-life of inhibition at the indicated concentration of inhibitor.

EXAMPLE 11

2-Fluoromethyl-2,5-diaminopentanoic acid and 2-fluoromethyl-2,6-diaminohexanoic acid were tested for inhibition of ornithine decarboxylase in rats according to the procedure of C. Danzin et al., *Life Sciences*, 24, 519 (1979). The results obtained are set forth in TABLES II, III, and IV, below:

TABLE II

ODC Activity remaining in ventral prostate, 5 hours after a single i.p. injection of 2-fluoromethyl-2,5-diaminopentanoic acid

| Dose | % Control |
|---|---|
| Control | 100 ± 11 |
| 12.5 mg/kg | 70.5 ± 12.5 |
| 25 mg/kg | 77.0 ± 10.5 |
| 50 mg/kg | 57.0 ± 13.0 |
| 100 mg/kg | 14.5 ± 10.0 |
| 200 mg/kg | 15.5 ± 1.0 |

TABLE III

ODC Activity remaining in ventral prostate and thymus, 6 hours after a single oral dose of 2-fluoromethyl-2,5-diaminopentanoic acid

| Dose | % Control Ventral Prostate | % Control Thymus |
|---|---|---|
| Control | 100 ± 8 | 100 ± 6 |
| 12.5 mg/kg | 98 ± 18 | 81 ± 6 |
| 25 mg/kg | 67 ± 7 | 93 ± 8 |
| 50 mg/kg | 45 ± 7 | 99 ± 5 |
| 100 mg/kg | 44 ± 6 | 87 ± 6 |

TABLE IV

ODC Activity remaining in ventral prostate after a single oral dose (200 mg/kg) of 2-fluoromethyl-2,6-diaminohexanoic acid (Animals were killed at various times after injection)

| Time (h) | % Control |
|---|---|
| Control | 100 ± 7 |
| 3 | 66 ± 6 |
| 6 | 44 ± 10 |
| 12 | 74 ± 7 |

EXAMPLE 12

2-Fluoromethyl-2,5-diaminopentanoic acid (MFM) was tested for contragestational activity in mice according to the procedure of J. Fozard et al., *Eur. J. Pharmacol.*, 65, 379 (1980).

In this experiment, the compound was given at the doses stated, subcutaneously (s.c.), every 6 hours starting at 12:00 on day 8 of gestation (4 doses). Animals were autopsied on day 18 and the numbers of viable feti and resorption nodules recorded. The results are shown below in TABLE V:

TABLE V

| Treatment | Dose mg/kg | Viable feti gravid female | Resorption nodules gravid female | n |
|---|---|---|---|---|
| Saline | — | 11.0 ± 0.5 | 3.0 ± 0.6 | 5 |
| MFMO | 50 | 9.1 ± 1.5 | 3.3 ± 1.1 | 8 |
|  | 100 | 12.7 ± 0.9 | 2.3 ± 0.6 | 7 |
|  | 200 | 9.2 ± 1.5 | 4.2 ± 1.2 | 10 |
|  | 400 | 5.4 ± 1.5 | 8.9 ± 1.9 | 11 |

The above data indicated that MFMO has contragestational activity in the mouse when administered s.c. every six hours on day 8 of gestation. The $ED_{50}$ is approximately 400 mg/kg (=1.6 g/kg/day). By extrapolation, a dose of 800 mg/kg (=3.2 g/kg/day) would be required to approach complete inhibition of fetal development.

EXAMPLE 13

2-Fluoromethyl-2,5-diaminopentanoic acid was tested for its effect on prostatic growth in rats according to the procedure of C. Danzin et al., *Biochem. J.*, 202, 175 (1982). The results obtained are given in TABLE VI, below:

TABLE VI

Effect of 2-fluoromethyl-2,5-diaminopentanoic acid on prostatic growth in rats after oral administration for 3 days

| Dose (g/l) | % Weight loss of prostate |
|---|---|
| 0 | 0 |
| 3.75 | −10 |
| 7.5 | −14 |
| 15 | −19 |

(a) Administered dissolved in drinking water employed as only water source for the animals.

EXAMPLE 14

2-Fluoromethyl-2,5-diaminopentanoic acid (MFMO) was tested for in vitro inhibition of ornithine decarboxylase from *Escherichia coli* and from *Pseudomonas aeruginosa* according to the procedure described as follows:

*Escherichia coli* (M.R.C. 59) and *Pseudomonas aeruginosa* (A.T.C.C. 9027) were grown as described by Kallio et al., *Biochem. J.*, 200, 69 (1981) in minimal medium [Davis et al., *J. Bacteriol.*, 60, 17 (1950)] at 37° C. Cells were harvested by centrifugation (10 minutes at 10,000 g) and washed once with phosphate-buffered saline, pH 7.2 (0.125M NaCl, 10 mM $Na_2HPO_4$, and 3 mM $KH_2PO_4$). The cell pellet was suspended in 10 mM Tris/HCl (pH 7.5) containing 1 mM dithiothreitol and 0.1 mM EDTA and disrupted by sonication with a Branson Cell Disruptor 350 (5×30 sec, setting 3). Cell debris was removed by centrifugation at 25,000 g for 30 minutes and the supernatant (approximately 16 mg protein/ml), used for the measurement of ornithine decarboxylase, was stored frozen at −20° C. without appreciable loss of activity.

Ornithine decarboxylase activity was measured by the release of $^{14}CO_2$. Assays contained 100 mM tris/HCl (pH 8.25 for *E. coli* and pH 7.5 for *P. aeruginosa*), 0.04 mM pyridoxal phosphate, 1mM dithiotheritol, 10 mM L-ornithine, 2.5 μCi D,L-[1-$^{14}$C]ornithine and 80–120 μg bacterial protein in a total volume of 1 ml. The reaction was run for 30 minutes at 37° C., terminated by adding 1 ml of 40% trichloroacetic acid, and $^{14}CO_2$ was trapped on filter paper saturated with 50 μl of methylbenzethonium hydroxide.

Time dependent irreversible inhibition of ornithine decarboxylase was determined according to the method of Kallio et al., *Biochem. J.*, 200, 69 (1981). The enzyme was incubated at 20° C. in 100 mM Tris/HCl (pH 8.25 for *E. coli* and pH 7.5 for *P. aeruginosa*) containing 1 mM DTT and 0.04 mM pyridoxal phosphate and various concentrations of MFMO. At selected times, 20 μl aliquots of the enzyme incubate were removed and transferred to the reaction flasks in which ODC activity was determined. These flasks contained all the components listed above for the ODc reaction (including 10 mM ornithine) except D,L-[1-$^{14}$C]ornithine. The flasks were kept on ice until all time points were taken and then D,L-[1-$^{14}$C]-ornithine was added and ODC activity was determined at 37° C. The transfer of the enzyme incubate to the reaction flask on ice resulted in a 45-fold dilution of the inhibitor and effectively stopped any further inhibition. Proteins were estimated by the method of Bradford, *Analyt. Biochem.*, 72, 248 (1976).

The results obtained are set forth in TABLE VII, below:

TABLE VII

Kinetic constants for 4-fluoromethyl-2,5-diaminopentanoic acid of time-dependent inhibition of bacterial ODC (in vitro)

| *E. coli* ODC |  |
|---|---|
| $K_I$ (mM) | 0.36 |
| $T_{\frac{1}{2}}$ (min) | 12 |
| *P. aeruginosa* ODC |  |
| $K_I$ (mM) | 0.30 |
| $T_{\frac{1}{2}}$ (min) | 12 |

Kinetic parameters for the inhibition of ODC were determined as described by Kitz, *J. Biol. Chem.*, 237, 3245 (1962) as modified by Jung et al., *Biochem. Biophys. Res. Comm.*, 67, 301 (1975). Concentrations of MFMO were between 0.02 and 1 mM. $K_I$ is the concentration of compound which gives half-maximal rate of inhibition and $T_{\frac{1}{2}}$ (min) is the half-life in minutes at infinite concentrations.

2-Fluoromethyl-2,5-diaminopentanoic acid was also found to inhibit *E. coli* ODC activity (99 % inhibition) when the bacteria were grown in the presence of 2 mM of the compound.

EXAMPLE 15

2-Fluoromethyl-2,5-diaminopentanoic acid (MFMO) in combination with 2-difuloromethyl-2-amino-5-guanidinopentanoic acid (DFMA) and dicyclohexylammonium sulfate (DCHA) were tested for their ability to restrict the growth of bacteria according to the following test procedure:

*E. coli* (M.R.C; 59) and *P. aeruginosa* (A.T.C.C. 9027) were grown as described by Kallio et al., *Biochem. J.*, 200, 69 (1981) on minimal medium [See Davis et al., *J.*

Bacteriol., 60, 17 (1950)] at 37° C. Growth was monitored in control and drug-treated cultures by measuring the absorbance of cell suspensions at 500 nm. Numbers of cells were determined using previously prepared standard curves plotting absorbance at 550 nm vs. number of viable cells. Generation times were calculated as described by Stainer et al., *The Microbial World*, 4th Ed., Prenture-Hall, N.J., pp 276-277. To determine polyamine content, the cells were harvested by centrifugation (10,000 g, 10 min), washed once with phosphate-buffered saline, pH 7.2 (0.125 M NaCl, 10 mM Na$_2$HPO$_4$ and 3 mM KH$_2$PO$_4$) and extracted overnight with 0.4 ml of 0.4 M perchloric acid. Proteins were removed by filtration on Millipore membranes (0.22 $\mu$m) and 20 $\mu$l aliquots of the filtrates were analyzed for polyamines with a Dionex D-300 Amino Acid Analyzer using a Dionex P/N 30831 column. After separation, polymines were derivatized with o-phthaldialdehyde and detected by fluorescence spectrometry. Buffers for elution and detection of polyamines were as described by Kallio et al., *Biochem. J.*, in press.

Incubation of *E. coli* and *P. aeruginosa* according to the above procedure in the presence of the three compounds (2 mM MFMO, 2.5 mM DFMA, 5 or 10 mM DCHA for *P. aeruginosa* and *E. coli*, respectively) resulted in a measurable increase in exponential growth phase generation times (decreased growth rates) of 40 and 70 %, respectively. As a consequence, the number of cells was markedly decreased. There was a three-fold decrease in the number of *E. coli* and greater than a six-fold decrease in the number of *P. aeruginosa* during the exponential phase of the growth curve. The inhibitory effects of the drug combination were completely reversed by the addition of 0.1 mM putrescine and 0.1 mM spermidine to the growth medium along with the drug combination.

Polyamine levels were dramatically affected by the drug treatments and the changes correlated well with changes in growth. It is apparently necessary to reduce both putrescine and spermidine concentrations to inhibit growth in these bacteria. Incubation with the three compounds in combination resulted in significantly reduced putrescine and spermidine levels in both bacteria and consequently the generation times of both bacteria were increased and cell numbers were appreciably decreased.

What is claimed is:

1. A method for preparing a compound of the formula:

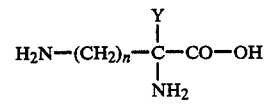

wherein n is 3 or 4; Y is —CH$_2$F or —CH$_2$Cl; which comprises:

(a) treating a compound of the formula

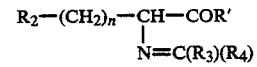

wherein n is as defined above, R' is (C$_1$-C$_8$)alkoxy, R$_3$ is hydrogen, phenyl, (C$_1$-C$_4$)alkyl, methoxy or ethoxy, R$_4$ is phenyl or (C$_1$-C$_4$)alkyl, or R$_3$ and R$_4$ taken together form —CH$_2$—(CH$_2$)$_m$—CH$_2$— wherein m is an integer of from 3 to 5, and R$_2$ is a group of the formula

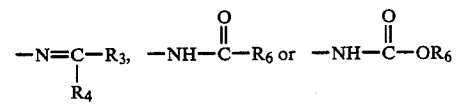

wherein R$_6$ is phenyl, benzyl or (C$_1$-C$_4$)alkyl and R$_3$ and R$_4$ are as defined above, with a strong base to form the corresponding carbanion;

(b) reacting the carbanion with an alkylating agent of the formula X$_1$CH$_2$X, wherein X$_1$ is fluorine or chlorine and X is chlorine, bromine or iodine, in an aprotic solvent in the presence of hexamethylphosphoramide at a temperature of about −120° C. to 120° C. and a reaction time of about ½ hour to 48 hours; and (c) hydrolyzing the alkylated product.

2. A method as defined in claim 1 for preparing 2-fluoromethyl-2,5-diaminopentanoic acid wherein the protected 2,5-diaminopentanoic acid employed in Step (a) is a (C$_1$-C$_8$)alkyl ester of 2,5-bis(benzylideneamino)-pentanoate, and the alkylating agent employed in Step (b) is chlorofluoromethane, bromofluoromethane, or iodofluoromethane.

3. A method as defined in claim 2 wherein the (C$_1$-C$_8$)alkyl ester is the methyl ester.

4. A method as defined in claim 2 or 3 wherein the strong acid employed in Step (a) is sodium tert-butoxide and the alkylating agent employed in Step (b) is chlorofluoromethane.

* * * * *

UNITED STATES PATENT AND TRADEMARK OFFICE
CERTIFICATE OF CORRECTION

PATENT NO. : 4,866,206
DATED : September 12, 1989
INVENTOR(S) : Philippe Bey and Michel Jung It is certified that error appears in the above-identified patent and that said Letters Patent is hereby corrected as shown below:

At column 2, line 26, the patent reads "when A" and should read --when Z--.

At column 3, line 32, the patent reads " "α-MFM" " and should read --α-MFMO--.

At column 4, line 37, the patent reads "diminopentanoate" and should read --diaminopentanoate--.

At column 5, line 15, the patent reads "-2,5-" and should read -- -2,6- --.

At column 5, line 18, the patent reads "MFM)" and should read -- MFMO)--.

At column 5, line 21, the patent reads "carboxylase" and should read --decarboxylase--.

At column 5, line 63, the patent reads "(α-gluoro-methylarginine)" and should read --(α-fluoromethylarginine)--.

At column 5, line 66, the patent reads "2-fluoromethyl 2,5-diaminpentanoic" and should read -- 2-fluoromethyl-2,5-diaminopentanoic --.

At column 8, line 31, the patent reads "2,2-diethylbutan-1-al," and should read -- 2,2-diethylbutan-1-al. --.

At column 9, line 60, the patent reads "(formula VIIIa) from methyl 2,5-bix" and should read -- (Formula VIIIa) from methyl 2,5-bis--.

At column 9, line 64, the patent reads "2-fluontanoic" and should read -- 2-fluoromethylpentanoic--.

At column 10, line 12, the patent reads "5-benzyloxy-pentanentrile" and should read -- 5-benzyloxypentanenitrile--.

UNITED STATES PATENT AND TRADEMARK OFFICE
CERTIFICATE OF CORRECTION

PATENT NO. : 4,866,206
DATED : September 12, 1989
INVENTOR(S) : Phillippe Bey and Michel Jung It is certified that error appears in the above-identified patent and that said Letters Patent is hereby corrected as shown below:

At column 10, line 17, the patent reads "herein Examples" and should read --herein in Examples--.

At column 11, line 23, the patent reads "halide form the aimino" and should read --halide from the amino--.

At column 12, line 6, the patent reads "hydrozine" and should read --hydrazine--.

At column 12, line 20, the patent reads "presence is carried out in an inert solvent," and should read --presence of a coupling agent. The coupling reaction is carried out in an inert solvent,--.

At column 12, line 59, the patent reads "reaction housing" and should read --reaction using--.

At column 12, line 65, the patent reads "Iia" and should read --IIa--.

At column 13, line 56, the patent reads "compound" and should read --compounds--.

At column 15, line 44, the patent reads "diaminhexanoate" and should read --diaminohexanoate--.

At column 16, line 65, the patent reads "(1.4 ml or 1.94 or 1.94 X $10^{-1}$ mol)" and should read --(1.4 ml or 1.94 x $10^{-2}$ mol)--.

At column 17, line 23, the patent reads "20-chloromethyl" and should read -- 2-chloromethyl --.

At column 17, line 62, the patent reads "3.22 g" and should read --3.11 g--.

At column 18, line 10, the patent reads "(m,4,-$CH_2$]1 $CH_2$-)" and should read -- (m, 4, -$CH_2CH_2$-).

At column 18, line 13, the patent reads "-$CH_2$]1 F)." and should read --  -$CH_2F$) --.

UNITED STATES PATENT AND TRADEMARK OFFICE
CERTIFICATE OF CORRECTION

PATENT NO. : 4,866,206
DATED : September 12, 1989
INVENTOR(S) : Phillipe Bey and Michel Jung It is certified that error appears in the above-identified patent and that said Letters Patent is hereby corrected as shown below:

At column 18, line 19, the patent reads "of sodium in" and should read --of sodium) in--.

At column 18, line 44, the patent reads "(m4,-CH$_2$-)" and should read --(m, 4, -CH$_2$-)--.

At column 18, line 54, the patent reads "Perking" and should read --Perkin--.

At column 19, line 26, the patent reads "2-Fluoromethyl2-2phthalimido" and should read -- 2-Fluoromethyl-2-phthalimido --.

At column 19, line 37, the patent reads "66 Hz" and should read --46 Hz--.

At column 19, line 68, the patent reads "20fluoromethyl" and should read -- 2-fluoromethyl --.

At column 20, line 24, the patent reads "5-benzylxy-pentanenitrile" and should read -- 5-benzyloxypentanenitrile--.

At column 20, line 27, the patent reads "(1.110 at" and should read --(1.11) at--.

At column 22, line 47, the patent reads "benzyloxypentanenitrile fluoromethyl-2-phthalimido-5-benzyloxypentanenitrile as follows:" and should read --benzyloxypentanenitrile as follows: --.

At column 22, line 60, the patent reads "(200 1)" and should read -- (200 ml) --.

At column 23, line 1, the patent reads "CH$_3$CH" and should read --CH$_3$CN--.

At column 23, line 11, the patent reads "-2,5-diaminohexanoic" and should read -- -2,6-diaminohexanoic --.

UNITED STATES PATENT AND TRADEMARK OFFICE
CERTIFICATE OF CORRECTION

PATENT NO.   : 4,866,206
DATED        : September 12, 1989
INVENTOR(S)  : Phillipe Bey and Michel Jung It is certified that error appears in the above-identified patent and that said Letters Patent is hereby corrected as shown below:

At column 24, line 41, the patent reads "in dissolved" and should read --is dissolved--.

At column 24, line 49, the patent reads "$J_{BS}$" and should read --$J_{BX}$--.

At column 25, line 10, the patent reads " -6-iodoheanenitrile" and should read -- -6-iodohexanenitrile --.

At column 25, line 12, the patent reads " $J_{AX}=J_{H-F}=46 Hz$)," and should read -- =$J_{AX} = J_{BX} = J_{H-F} = 46$ Hz) --.

At column 27, line 1, the patent reads "(MFM)" and should read -- (MFMO) --.

At column 28, line 23, the patent reads "ODc" and should read --ODC--.

Signed and Sealed this

Nineteenth Day of March, 1991

Attest:

HARRY F. MANBECK, JR.

*Attesting Officer*     *Commissioner of Patents and Trademarks*